US011577090B2

(12) United States Patent
Etkin et al.

(10) Patent No.: US 11,577,090 B2
(45) Date of Patent: Feb. 14, 2023

(54) MACHINE LEARNING BASED ARTIFACT REJECTION FOR TRANSCRANIAL MAGNETIC STIMULATION ELECTROENCEPHALOGRAM

(71) Applicants: The Board of Trustees of the Leland Stanford Junior University, Stanford, CA (US); Department of Veterans Affairs, Washington, DC (US)

(72) Inventors: Amit Etkin, Palo Alto, CA (US); Corey Keller, Palo Alto, CA (US); Wei Wu, Palo Alto, CA (US)

(73) Assignees: The Board of Trustees of the Leland Stanford Junior University, Stanford, CA (US); Department of Veterans Affairs, Washington, DC (US)

( * ) Notice: Subject to any disclaimer, the term of this patent is extended or adjusted under 35 U.S.C. 154(b) by 858 days.

(21) Appl. No.: 16/470,946

(22) PCT Filed: Dec. 19, 2017

(86) PCT No.: PCT/US2017/067424
§ 371 (c)(1),
(2) Date: Jun. 18, 2019

(87) PCT Pub. No.: WO2018/118994
PCT Pub. Date: Jun. 28, 2018

(65) Prior Publication Data
US 2020/0054888 A1 Feb. 20, 2020

Related U.S. Application Data

(60) Provisional application No. 62/436,249, filed on Dec. 19, 2016.

(51) Int. Cl.
*A61N 2/00* (2006.01)
*A61B 5/00* (2006.01)
(Continued)

(52) U.S. Cl.
CPC ............. *A61N 2/006* (2013.01); *A61B 5/316* (2021.01); *A61B 5/377* (2021.01); *A61B 5/726* (2013.01);
(Continued)

(58) Field of Classification Search
CPC ..... A61B 5/7207; A61B 5/726; A61B 5/7217; A61B 5/316; A61B 5/7267; A61B 5/377;
(Continued)

(56) References Cited

U.S. PATENT DOCUMENTS

| 2005/0043774 A1* | 2/2005 | Devlin ................. A61B 5/6814 |
| | | 607/45 |
| 2007/0032737 A1 | 2/2007 | Causevic et al. |
| 2012/0203079 A1 | 8/2012 | McLaughlin |

OTHER PUBLICATIONS

Irene Winkler, Stefan Haufe, and Michael Tangermann. Automatic Classification of Artifactual ICA-Components for Artifact Removal in EEG Signals, 2011, Behavioral and Brain Functions, 7:30 http://www.behavioralandbrainfunctions.con/content/7/1/30 (Year: 2011).*

(Continued)

*Primary Examiner* — Christine H Matthews
*Assistant Examiner* — Joshua Daryl D Lannu
(74) *Attorney, Agent, or Firm* — Mintz Levin Cohn Ferris Glovsky and Popeo, P.C.

(57) ABSTRACT

A method for machine learning based artifact rejection is provided. The method may include applying a machine learning model to identify artefactual independent components in transcranial magnetic stimulation electroencephalogram data collected during a transcranial magnetic stimulation procedure. Clean transcranial magnetic stimulation electroencephalogram data is generated by removing, from the transcranial magnetic stimulation electroencephalogram data, the artefactual independent components. Real-time adjustments to parameters of the transcranial magnetic stimulation procedure may be performed based on the clean transcranial magnetic stimulation electroencephalogram data. Related systems and articles of manufacture, including computer program products, are also provided.

35 Claims, 11 Drawing Sheets

(51) Int. Cl.
  *G06N 7/00*    (2006.01)
  *A61B 5/316*   (2021.01)
  *A61B 5/377*   (2021.01)

(52) U.S. Cl.
  CPC .......... *A61B 5/7217* (2013.01); *A61B 5/7267* (2013.01); *G06N 7/00* (2013.01)

(58) Field of Classification Search
  CPC ........ A61B 5/374; A61B 5/4836; A61N 2/02; A61N 2/006; G06N 7/00
  See application file for complete search history.

(56) References Cited

OTHER PUBLICATIONS

Winkler et al., "Automatic Classification of Artifactual ICA-Components for Artifact Removal in EEG Signals" Behavioral and Brain Functions 7.1 (2011): 30, Abstract, p. 9, 12 [online] URL= <https://behavioralandbrainfunctions.biomedcentral.com/track/pdf/10.1186/1744-9081-7-30?site=behavioralandbrainfunctions.biomedcentral.com>.
Parra et al., "Recipes for the linear analysis of EEG." NeuroImage 28 (2005) 326-341 (2005), entire document [online] URL <http://bme.ccny.cuny.edu/faculty/lparra/publish/ParraSpenceGersonSajda2005.pdf.

* cited by examiner

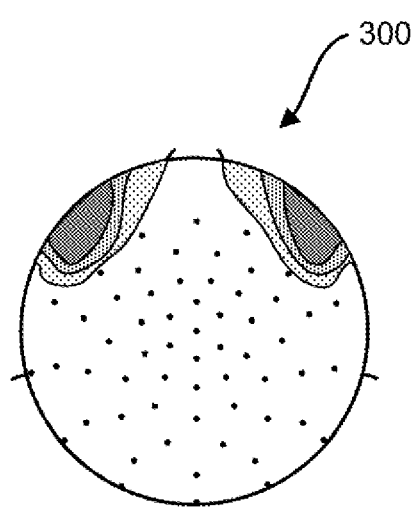
FIG. 3A
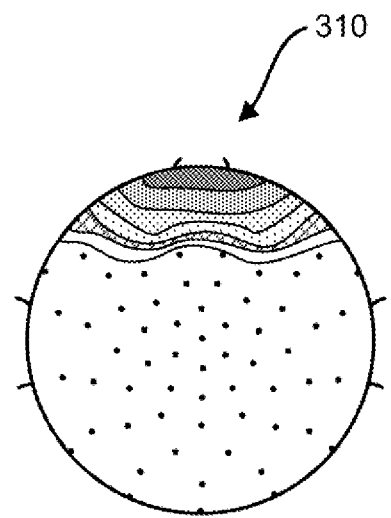
FIG. 3B
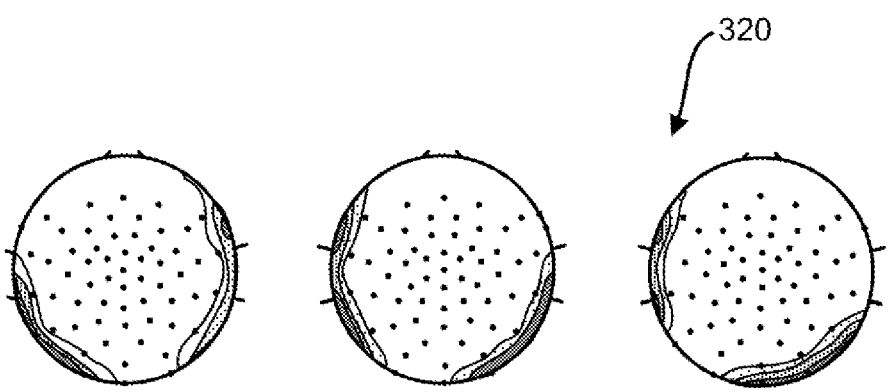
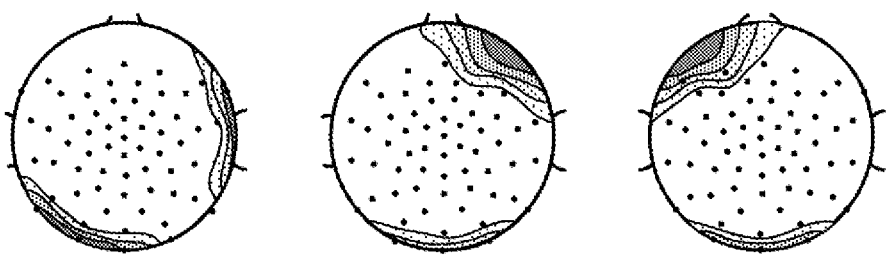
FIG. 3C

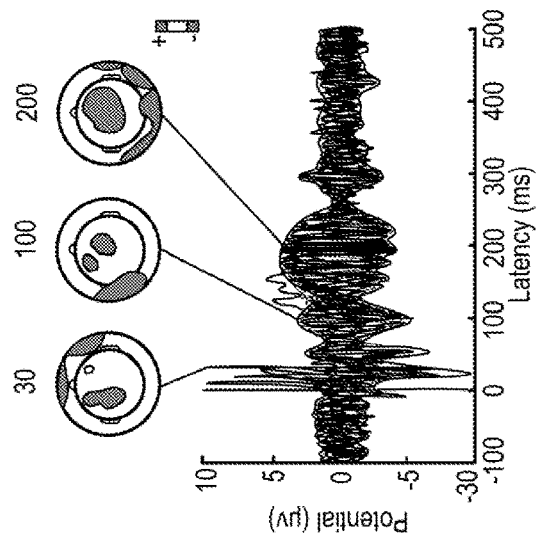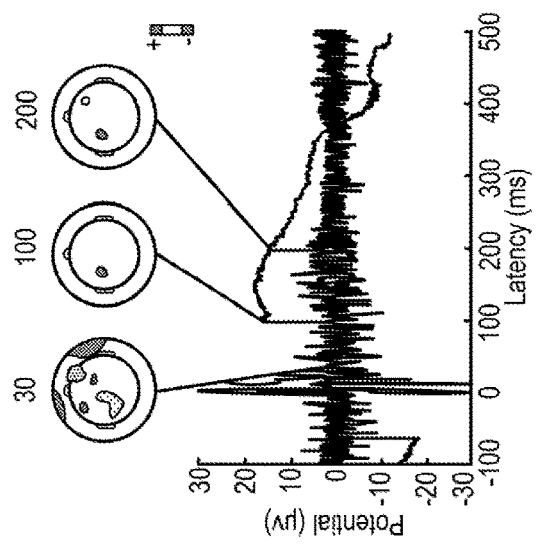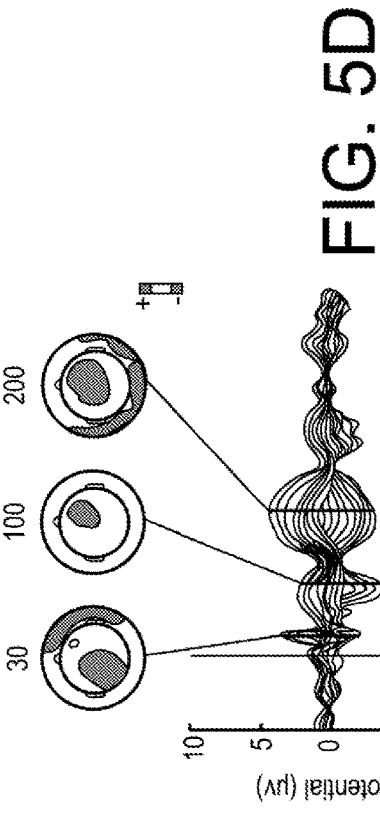

| Methods | Left M1 | Right M1 | V1 | Left pDLPFC | Right pDLPFC | Left aDLPFC | Right aDLPFC | Left FEF | Right FEF |
|---|---|---|---|---|---|---|---|---|---|
| ARTIST | 95.88 | 90.12 | 98.77 | 92.90 | 95.60 | 97.18 | 98.58 | 97.56 | 95.80 |
| MARA | 94.71 | 88.89 | 94.48 | 90.16 | 93.71 | 95.48 | 95.74 | 93.29 | 94.41 |

| Methods | Left IPL | Right IPL | Left IPS | Right IPS | Left ANG | Right ANG | mean ± std |
|---|---|---|---|---|---|---|---|
| ARTIST | 97.10 | 92.52 | 96.27 | 96.32 | 95.24 | 98.28 | 95.78 ± 2.41 |
| MARA | 95.65 | 90.65 | 91.79 | 89.71 | 95.24 | 93.10 | 93.14 ± 2.33 |

FIG. 6B

MACHINE LEARNING BASED ARTIFACT REJECTION FOR TRANSCRANIAL MAGNETIC STIMULATION ELECTROENCEPHALOGRAM

CROSS-REFERENCE TO RELATED APPLICATION

This application is a national phase entry of Patent Cooperation Treaty Application PCT/US2017/06724 filed Dec. 19, 2017, entitled "MACHINE LEARNING BASED ARTIFACT REJECTION FOR TRANSCRANIAL MAGNETIC STIMULATION ELECTROENCEPHALOGRAM," which claims priority to U.S. Provisional Application No. 62/436,249, filed on Dec. 19, 2016 and entitled AUTOMATED ARTIFACT REJECTION FOR TRANSCRANIAL MAGNETIC STIMULATION ELECTROENCEPHALOGRAM DATA, the disclosure of these are incorporated herein by reference in their entirety.

FIELD

The subject matter described herein relates generally to signal processing and more specifically to the rejection of artifacts from electroencephalogram signals associated with the application of transcranial magnetic stimulation.

BACKGROUND

Transcranial magnetic stimulation (TMS) is a non-invasive procedure during which a magnetic field generator (e.g., a coil) may be positioned near the head of a subject such that the magnetic field generated by the coil induces corresponding electrical currents in a region of the subject's brain directly beneath the coil. For single pulse transcranial magnetic stimulation (spTMS), the transcranial magnetic stimulation may be administered to the subject a single stimulus (e.g., magnetic pulse) at a time. However, the stimulus for transcranial magnetic stimulation may also be applied in multiples (e.g., in pairs and/or in trains) during other types of transcranial magnetic stimulation procedure such as, for example, paired-pulse transcranial magnetic stimulation (ppTMS), repetitive transcranial magnetic stimulation (rTMS), and/or the like. The transcranial magnetic stimuli may cause, in the brain's neural signalling activities, a localized change that is capable of triggering a broader change in the neural signalling activities throughout the brain as a whole.

SUMMARY

In one aspect, there is provided a method for machine learning based artifact rejection. The method may include: applying a machine learning model to identify one or more artefactual independent components comprising transcranial magnetic stimulation electroencephalogram data collected during a transcranial magnetic stimulation procedure; generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, adjustments to one or more parameters of the transcranial magnetic stimulation procedure.

In some variations, one or more features disclosed herein including the following features can optionally be included in any feasible combination. The machine learning model may be a classifier. The machine learning model may be a Fisher linear discriminant analyzer. The transcranial magnetic stimulation electroencephalogram data may be decomposed into a plurality of independent components. Each of the plurality of independent components may be one of a plurality of non-Gaussian signals forming a multivariate signal corresponding to the transcranial magnetic stimulation electroencephalogram data. The transcranial magnetic stimulation electroencephalogram data may be preprocessed prior to being decomposed into the plurality of independent components.

In some variations, the preprocessing may include removing a portion of the transcranial magnetic stimulation electroencephalogram data that is recorded subsequent to the administration of one or more transcranial magnetic stimuli. The removed portion of the transcranial magnetic stimulation electroencephalogram data may be a 10-millisecond segment of the transcranial magnetic stimulation electroencephalogram data that is recorded subsequent to the administration of the one or more transcranial magnetic stimuli.

In some variations, the preprocessing may further include filtering the transcranial magnetic stimulation electroencephalogram data to remove spectrally irrelevant transcranial magnetic stimulation electroencephalogram data. The filtering of the transcranial magnetic stimulation electroencephalogram data may include applying a high-pass filter to at least remove low frequency transcranial magnetic stimulation electroencephalogram data associated with slow drifts. The high-pass filter may be a 0.01 Hertz zero-phase infinite impulse filter. The filtering of the transcranial magnetic stimulation electroencephalogram data may include applying a multi-taper regression technique to at least identify, via a Thompson F-statistic, high frequency transcranial magnetic stimulation electroencephalogram data associated with alternating current line noise.

In some variations, the preprocessing may further include epoching the transcranial magnetic stimulation electroencephalogram data and/or re-referencing the transcranial magnetic stimulation electroencephalogram data with respect to a common average.

In some variations, a feature vector corresponding to an independent component from a plurality of independent components comprising the transcranial magnetic stimulation electroencephalogram data may be generated. The machine learning model may be trained to determine, based on the feature vector associated with the independent component, whether the independent component is artefactual or non-artefactual. The machine learning model may be trained based at least on training data including one or more independent components having known classifications as an artefactual independent component and/or a non-artefactual independent components.

In some variations, the feature vector may include a spatial range feature corresponding to an absolute difference between a maximum and minimum voltage differential present in a scalp map associated with the independent component.

In some variations, the feature vector may include a regional activation feature corresponding to an absolute value of an average voltage differential recorded within one or more specific regions of a scalp map associated with the independent component. The one or more specific regions may include a central, frontal, occipital and/or temporal region of a brain.

In some variations, the feature vector may include a border activation feature corresponding to whether an electrode recording the highest voltage differential in a scalp map associated with the independent component is located on a border of the scalp map.

In some variations, the feature vector may include a horizontal eye movement feature corresponding to a result of a comparison between a scalp map associated with the independent component and a template scalp map associated with horizontal eye movement, the result of the comparison comprising an absolute correlation coefficient indicative of a degree of correspondence between the scalp map of the independent component and the template scalp map for horizontal eye movement.

In some variations, the feature vector may include an eye blinking feature corresponding to a result of a comparison between a scalp map associated with the independent component and a template scalp map associated with eye blinking movements, the result of the comparison comprising an absolute correlation coefficient indicative of a degree of correspondence between the scalp map of the independent component and the template scalp map for eye blinking movements. The eye blinking movement may include transcranial magnetic stimulation-evoked eye blinking movements and/or voluntary eye blinking movements.

In some variations, the feature vector may include an electrocardiogram artifact feature corresponding to a result of a comparison between a scalp map associated with the independent component and a plurality of template scalp maps associated with cardiac contractions, the electrocardiogram artifact feature being a value indicating whether a maximum correlation coefficient of the comparison between the scalp map for the independent component and the plurality of template scalp maps exceeds a threshold value.

In some variations, the feature vector may include an electrocardiogram temporal feature corresponding to whether a number of peaks present in the independent component exceeds a threshold value. The independent component may be decomposed by at least applying a Daubechies least-asymmetric wavelet, the decomposing of the independent component enabling peak detection to be performed in a wavelet domain instead of a time domain.

In some variations, the feature vector may include a source activity features corresponding to a complexity of a source pattern associated with the independent component.

In some variations, the feature vector may include a maximum magnitude feature corresponding to a maximum voltage differential that is recorded across a plurality of trials of transcranial magnetic stimuli that are administered during the transcranial magnetic stimulation procedure. Each trial of transcranial magnetic stimuli may include an administration of a single transcranial magnetic stimulation pulse, a pair of transcranial magnetic stimulation pulses, or a train of transcranial magnetic stimulation pulses.

In some variations, the feature vector may include a short-time magnitude feature corresponding to one or more transcranial magnetic stimulation-evoked potential peaks present in the independent component. The one or more transcranial magnetic stimulation-evoked potential peaks may be identified by at least determining a mean magnitude of voltage differentials recorded over a plurality of time windows. The plurality of time windows may include a 0-60 millisecond time window, a 60-120 millisecond time window, and/or a 140-220 millisecond time window.

In some variations, the feature vector may include a skewness feature corresponding to a measure of asymmetry in a probability distribution of transcranial magnetic stimulation electroencephalogram data.

In some variations, the feature vector may include a band-power feature corresponding to a band-power for a theta band between 4 Hertz and 7 Hertz, an alpha band between 8 Hertz and 12 Hertz, a beta band between 13 Hertz and 30 Hertz, and/or a gamma band between 31 Hertz and 50 Hertz.

In some variations, the feature vector may include a first electroencephalogram spectral feature corresponding to a mean fit error between an actual spectrum of the independent component and a fitted shape of an electroencephalogram spectrum within an alpha band.

In some variations, the feature vector may include a first electroencephalogram spectral feature corresponding to a value of a parameter b in the following equation:

$$y = \frac{a}{f^b} + c(b > 0).$$

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to web application user interfaces, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 3A depicts a template scalp map associated with horizontal eye movements, in accordance with some example embodiments;

FIG. 3B depicts a template scalp map associated with blinking movements, in accordance with some example embodiments;

FIG. 3C depicts a collection of template scalp maps associated with cardiac contractions, in accordance with some example embodiments;

FIGS. 5A-D depict transcranial magnetic stimulation electroencephalogram data that has been subject to machine learning based artifact rejection, in accordance with some example embodiments;

FIG. 6B depicts a table illustrating the classification accuracies, in accordance with some example embodiments;

When practical, similar reference numbers denote similar structures, features, or elements.

DETAILED DESCRIPTION OF THE INVENTION

Figure 1:
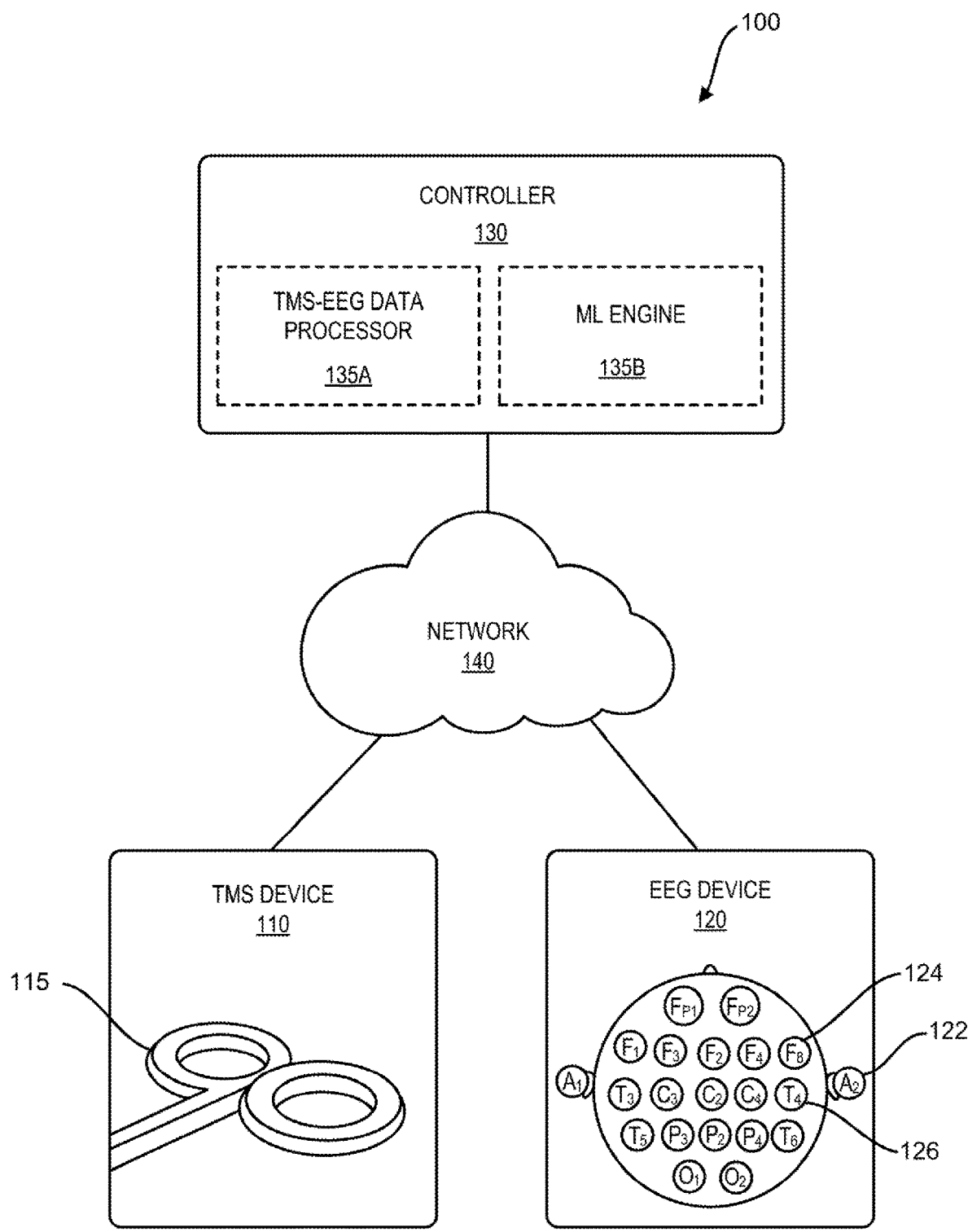
FIG. 1 depicts a transcranial magnetic stimulation electroencephalogram system, in accordance with some example embodiments.

Electroencephalogram (EEG) may be used to measure a brain's responses to one or more stimuli applied during a transcranial magnetic stimulation (transcranial magnetic stimulation) procedure. A typical electroencephalogram device may include a plurality of electrodes, which may be placed along the surface of the scalp and/or implanted beneath the scalp to record electrical activities within the brain. While transcranial magnetic stimulation may be an effective diagnostic and treatment tool for various disorders (e.g., depression, post traumatic stress disorder (PTSD), neuropathic pain), electroencephalogram measurements of the brain's immediate responses to one or more transcranial magnetic stimuli may provide real-time guidance during a transcranial magnetic stimulation procedure. For example, transcranial magnetic stimulation parameters including, for example, stimulation duration, stimulation frequency, stimulation magnitude, stimulation area, time interval between stimuli, and/or the like may be adjusted in real time based on the brain's responses to one or more transcranial magnetic stimuli. However, electroencephalogram data associated with transcranial magnetic stimulation (henceforth transcranial magnetic stimulation electroencephalogram data) tends to include a variety of artifacts that can skew subsequent analysis of the data. For instance, transcranial magnetic stimulation electroencephalogram data may include artifacts arising from the transcranial magnetic stimulus itself, subject motion (e.g., scalp muscle activation, eye blinks), coil clicks, coil recharge, and/or the like. As such, in some example embodiments, a transcranial magnetic stimulation electroencephalogram system may be configured to remove artifacts from transcranial magnetic stimulation electroencephalogram data.

In some example embodiments, a machine learning based technique for detecting and/or removing artifacts from transcranial magnetic stimulation electroencephalogram data may eliminate the inconsistencies that are typically associated with manual artifact rejection. For example, manual artifact rejection may rely on subjective judgments, which tend to vary from one technician to another. As such, the results for manual artifact rejection may be inconsistent. Moreover, manual ratification rejection is a time consuming process, which may prevent transcranial magnetic stimulation electroencephalogram data from being used for real-time guidance of transcranial magnetic stimulation procedures. That is, transcranial magnetic stimulation electroencephalogram data collected during a transcranial magnetic stimulation procedure cannot be manually processed fast enough for clean transcranial magnetic stimulation electroencephalogram data to be available during the transcranial magnetic stimulation procedure. As used herein, clean transcranial magnetic stimulation electroencephalogram data may refer to transcranial magnetic stimulation electroencephalogram data that has been subject to artifact rejection and is therefore free from various artifacts.

By contrast, machine learning based artifact rejection may generate clean transcranial magnetic stimulation electroencephalogram data at sufficient speed for clean transcranial magnetic stimulation electroencephalogram data to be available during the transcranial magnetic stimulation procedure. This clean transcranial magnetic stimulation electroencephalogram data, which may be more consistent than clean transcranial magnetic stimulation electroencephalogram data generated through manual artifact rejection, may be used to adjust the parameters of the transcranial magnetic stimulation procedure. For example, stimulation duration, stimulation frequency, stimulation magnitude, stimulation area, and/or time interval between stimuli may be changed, in real-time, based on the clean transcranial magnetic stimulation electroencephalogram data generated through machine learning based artifact rejection.

In some example embodiments, a transcranial magnetic stimulation electroencephalogram system may be configured to administer one or more types of transcranial magnetic stimulation procedures including, for example, single-pulse transcranial magnetic stimulation (spTMS), paired-pulse transcranial magnetic stimulation (ppTMS), repetitive transcranial magnetic stimulation (rTMS), and/or the like. Moreover, the transcranial magnetic stimulation electroencephalogram system may be configured to collect, during a transcranial magnetic stimulation treatment, corresponding transcranial magnetic stimulation electroencephalogram data indicative of a subject's responses to the transcranial magnetic stimuli that is being administered to the subject. According to some example embodiments, the transcranial magnetic stimulation electroencephalogram system may perform artifact rejection to remove, from the transcranial magnetic stimulation electroencephalogram data, artifacts originating from a variety of artefactual sources including, for example, the transcranial magnetic stimuli, subject motion (e.g., scalp muscle activation, eye blinks), coil clicks, coil recharge, and/or the like.

In order to remove artifacts from transcranial magnetic stimulation electroencephalogram data, the transcranial magnetic stimulation electroencephalogram system may decompose transcranial magnetic stimulation electroencephalogram data, which may be preprocessed (e.g., to remove transcranial magnetic stimulation artifacts and/or spectrally irrelevant artifacts), into a plurality of independent components (ICs). As used herein, an "independent component" may be one of the many independent non-Gaussian signals that form a multivariate signal corresponding to the transcranial magnetic stimulation electroencephalogram data. Each independent component may originate from a single source, which may be artefactual or non-artefactual.

The transcranial magnetic stimulation electroencephalogram system may apply one or more machine learning models (e.g., a classifier including, for example, a Fisher linear discriminant analysis classifier and/or the like) trained to identify artefactual independent components amongst the plurality of independent components. The artefactual independent components may be removed and the resulting clean transcranial magnetic stimulation electroencephalogram data may be used to provide real-time guidance during a transcranial magnetic stimulation procedure. For instance, the transcranial magnetic stimulation electroencephalogram system may perform, based on the clean transcranial magnetic stimulation electroencephalogram data, real-time adjustments to one or more treatment parameters including, for example, treatment duration, stimulation frequency, stimulation magnitude, stimulation area, time interval between stimuli, and/or the like.

FIG. 1 depicts a transcranial magnetic stimulation electroencephalogram system 100, in accordance with some example embodiments. Referring to FIG. 1, the transcranial magnetic stimulation electroencephalogram system 100 may include a transcranial magnetic stimulation device 110, an electroencephalogram device 120, and a controller 130. As shown in FIG. 1, the controller 130 may be coupled to the transcranial magnetic stimulation device 110 and the electroencephalogram device 120. For instance, the controller 130 may receive, from the electroencephalogram device 120, transcranial magnetic stimulation electroencephalogram data corresponding to a subject's responses to one or more transcranial magnetic stimuli administered by the transcranial magnetic stimulation device 110 during a transcranial magnetic stimulation procedure.

The controller 110 may be configured to perform artifact rejection to remove, during the transcranial magnetic stimulation procedure, artifacts from the transcranial magnetic stimulation electroencephalogram data. Moreover, the controller 110 may perform, based on the resulting clean transcranial magnetic stimulation electroencephalogram data, real-time adjustments to the parameters of the transcranial magnetic stimulation procedure. It should be appreciated that the controller 130 may be coupled to the transcranial magnetic stimulation device 110 and the electroencephalogram device 120 via any wired and/or wireless connections including, for example, over a network 140. The network 140 may be any wired and/or wireless network including, for example, a public land mobile network (PLMN), a local area network (LAN), a virtual local area network (VLAN), a wide area network (WAN), the Internet, and/or the like.

In some example embodiments, the transcranial magnetic stimulation device 110 may include a coil 115, which may serve as a magnetic field generator. During a transcranial magnetic stimulation treatment, the coil 115 may be positioned near the head of a subject and may generate one or more magnetic pulses that induce corresponding electrical currents in a region of the subject's brain directly beneath the coil 115. The effects of these electrical currents in stimulating the subject's brain may serve diagnostic and/or therapeutic purposes. For instance, changes in a subject's behaviors subsequent to the application of one or more transcranial magnetic stimuli to a specific site of the subject's brain may indicate a causal link between that site and certain behaviors. Alternately and/or additionally, transcranial magnetic stimuli may improve and/or relieve symptoms associated with a variety of disorders including, for example, depression, post traumatic stress disorder (PTSD), neuropathic pain.

The transcranial magnetic stimulation device 110 may be configured to administer one or more types of transcranial magnetic stimulation procedures including, for example, single pulse transcranial magnetic stimulation, paired pulse transcranial magnetic stimulation, repetitive transcranial magnetic stimulation, and/or the like. As such, the coil 115 may be configured to deliver, to a subject, a single, a pair, and/or a train of transcranial magnetic stimuli (e.g., magnetic pulses) at a time. As used herein, a "trial" may refer to the single, pair, and/or train of transcranial magnetic stimuli that is administered to the subject at a time. It should be appreciated that single transcranial magnetic stimulation procedure or session may include the administration of any number of trials of transcranial magnetic stimuli.

In some example embodiments, the electroencephalogram device 120 may include a plurality of electrodes including, for example, a first electrode 122, a second electrode 124, and a third electrode 126. The plurality of electrodes (e.g., the first electrode 122, the second electrode 124, and the third electrode 126) may be configured to measure electrical activities within the brain of a subject. To do so, the electrodes may be placed along the surface of the scalp of the subject and/or implanted beneath the scalp. According to some example embodiments, the electroencephalogram device 120 may be configured to measure electrical activities that have been triggered by one or more transcranial magnetic stimuli (e.g., administered by the transcranial magnetic stimulation device 110). Referring again to FIG. 1, the first electrode 122 may serve as a reference electrode while the second electrode 124 and/or the third electrode 126 may each serve as a recording electrode.

As used herein, a "channel" may refer to the recorded voltage differential between a reference electrode and a recording electrode. For instance, the electroencephalogram device 120 may provide a first channel that records the voltage differential between the first electrode 122 and the second electrode 124 as well as a second channel that records the voltage differential between the first electrode 122 and the third electrode 126. The voltage differential recorded at every channel (e.g., the first channel and the second channel) of the electroencephalogram device 120 at a particular point in time $t_i$ may be mapped to a corresponding scalp map showing a spatial distribution of the voltage differentials measured across the entire scalp of the subject at that particular time $t_i$. Meanwhile, the waveform associated with a particular channel (e.g., the first channel or the second channel) may reflect the temporal distribution of voltage differentials over that channel across a certain period of time. A montage may refer to a collection of waveforms that may include the waveforms of every channel (e.g., the first channel and the second channel) present in electroencephalogram device 120.

Figure 2:
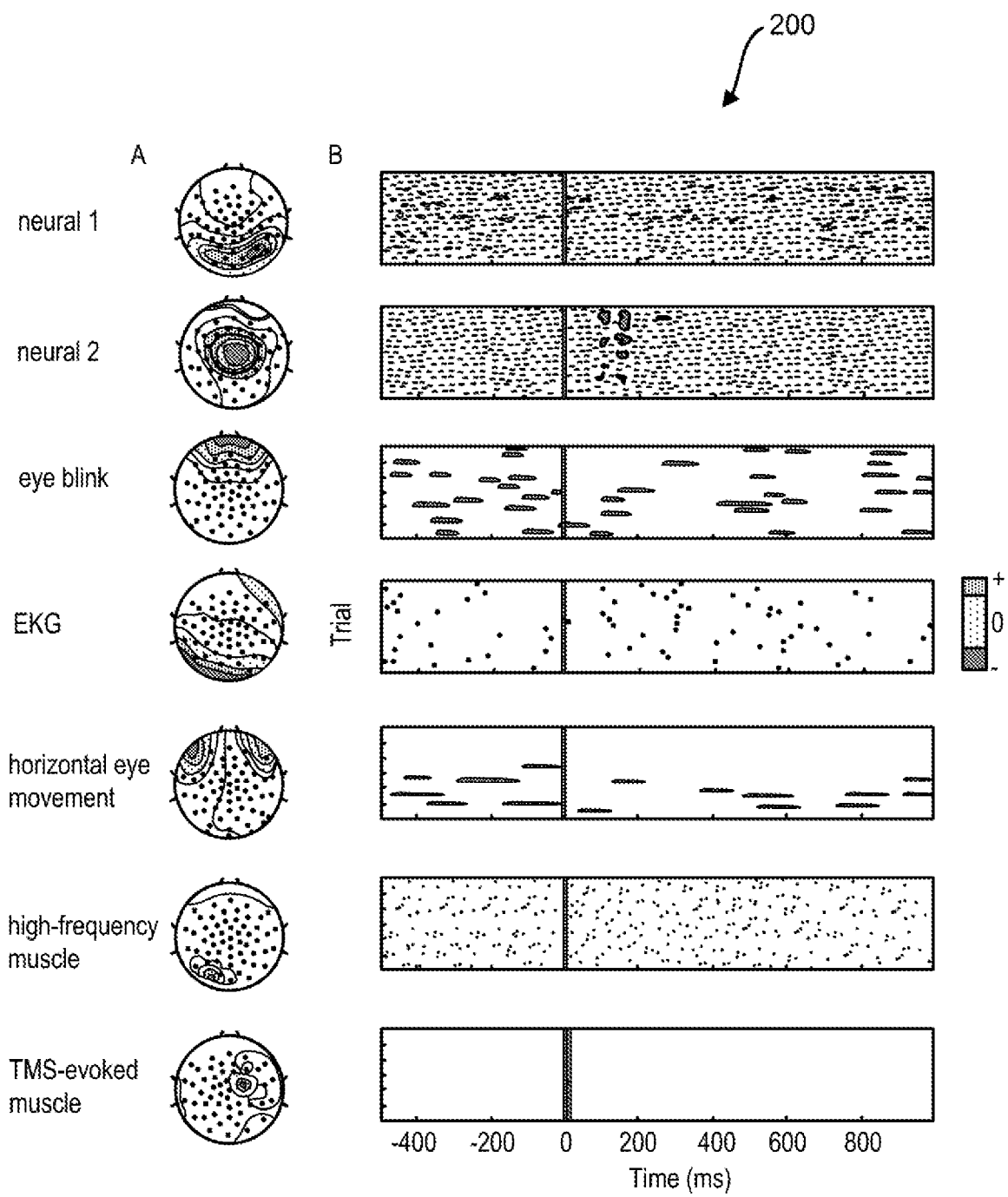
FIG. 2 depicts neural and non-neural components of transcranial magnetic stimulation electroencephalogram data, in accordance with some example embodiments.

FIG. 2 depicts neural and non-neural components of transcranial magnetic stimulation electroencephalogram data, in accordance with some example embodiments. Referring to FIG. 2, scalp maps showing the activation of various electrodes as well as the magnitudes of the voltage differential recorded at each electrode are shown in column A. The corresponding montages for the voltage differentials that are recorded at each electrode (e.g., in the electroencephalogram device 120) over a time period of −400 millisecond to 800 millisecond are shown in column B. It should be appreciated that at one or more transcranial magnetic stimuli may be administered (e.g., by the transcranial magnetic stimulation device 110) at 0 ms. The different scalp maps and montages respectively depict the spatial and temporal distribution of voltage differentials recorded at each electrode (e.g., in the electroencephalogram device 120). These voltage differentials may arise from a plurality of different artefactual and non-artefactual sources. For instance, FIG. 2 shows the scalp map and montages associated with two neural sources (e.g., neural 1 and neural 2) as well as artefactual sources including, for example, subject eye blink, cardiac contractions, horizontal eye movement, high-frequency muscle movements, transcranial magnetic stimulation-evoked muscle movements, and/or the like.

In some example embodiments, the controller 130 may be configured to control the operations of the transcranial magnetic stimulation device 110 including by performing real-time adjustments to one or more transcranial magnetic stimulation parameters including, for example, stimulation duration, stimulation frequency, stimulation magnitude, stimulation area, time interval between stimuli, and/or the like. As shown in FIG. 1, the controller 130 may include a transcranial magnetic stimulation electroencephalogram data processor 135A and a machine learning engine 135B.

The transcranial magnetic stimulation electroencephalogram data processor 135A may be configured to perform machine learning based artifact rejection to remove, from the transcranial magnetic stimulation electroencephalogram data collected by the electroencephalogram device 120, one or more artifacts that may skew this transcranial magnetic stimulation electroencephalogram data. The transcranial magnetic stimulation electroencephalogram data collected by the electroencephalogram device 120 may correspond to electrical activities triggered by one or more transcranial magnetic stimuli administered by the transcranial magnetic stimulation device 110.

Meanwhile, the machine learning models used by the transcranial magnetic stimulation electroencephalogram data processor 135A to perform artifact rejection may be trained and provided by the machine learning engine 135B. For example, the machine learning engine 135B may train one or more machine learning models including, for example, classifiers, neural networks, and/or the like, to perform artifact rejection including, for example, by identifying artefactual independent components originating from artefactual sources. Artifact rejection may include removing, from the raw transcranial magnetic stimulation electroencephalogram data recorded by the electroencephalogram device 120, the artefactual independent components identified by the trained machine learning models provided by the machine learning engine 135B. As shown in FIG. 1, the training of machine learning models may be performed locally at the controller 130, for example, by the machine learning engine 135B. However, it should be appreciated that the training of machine learning models may be performed elsewhere, for example, at a remote computing system, and the trained machine learning models may be deployed as computer software and delivered to the controller 130, for example, via the network 140.

According to some example embodiments, real-time adjustments of one or more transcranial magnetic stimulation parameters may be performed based on the resulting clean transcranial magnetic stimulation electroencephalogram data. Adjusting one or more transcranial magnetic stimulation parameters in real-time may include changing the existing transcranial magnetic stimulation parameters associated with one or more previously administered transcranial magnetic stimuli such that one or more subsequent transcranial magnetic stimuli may be administered with different transcranial magnetic stimulation parameters. For example, one or more subsequent transcranial magnetic stimuli may be administered with a different stimulation duration, stimulation frequency, stimulation magnitude, stimulation area, time interval between stimuli, and/or the like.

In some example embodiments, the transcranial magnetic stimulation electroencephalogram data processor 135A may preprocess the transcranial magnetic stimulation electroencephalogram data received from the electroencephalogram device 120 for machine learning based artifact rejection. This preprocessing of the transcranial magnetic stimulation electroencephalogram data may include the removal of artifacts associated with the one or more transcranial magnetic stimuli that was delivered by the transcranial magnetic stimulation device 110. Thus, the processing of the transcranial magnetic stimulation electroencephalogram data may include removing transcranial magnetic stimulation electroencephalogram data recorded immediately subsequent to the administration of one or more transcranial magnetic stimuli (e.g., by the transcranial magnetic stimulation device 110). For example, the transcranial magnetic stimulation electroencephalogram data processor 135A may be configured to discard transcranial magnetic stimulation electroencephalogram data that is recorded up to 10 milliseconds (ms) after the administration of one or more transcranial magnetic stimuli.

The preprocessing of the transcranial magnetic stimulation electroencephalogram data may also include removing decay artifacts. It should be appreciated that applying a frequency filter to transcranial magnetic stimulation electroencephalogram data containing decay artifacts may induce Gibbs phenomenon, which refers to ringing artifacts in the nearby time period. As such, in some example embodiments, the removal of decay artifacts may be performed prior to applying, to the transcranial magnetic stimulation electroencephalogram data, frequency filters to remove, for example, spectrally irrelevant artifacts.

To remove decay artifacts, the transcranial magnetic stimulation electroencephalogram data processor 135A may remove portions of the transcranial magnetic stimulation electroencephalogram data associated with slow direct current drift. Moreover, the transcranial magnetic stimulation electroencephalogram data processor 135A may perform independent component analysis (ICA) on the transcranial magnetic stimulation electroencephalogram data. For example, performing the independent component analysis may remove, from the transcranial magnetic stimulation electroencephalogram data, independent components with mean magnitude exceeding a threshold value (e.g., 30 microvolts) from electroencephalogram data recorded up to 50 milliseconds after the administration of transcranial magnetic stimulation.

Equation (1) below corresponds to the generative model defined by the independent component analysis of the transcranial magnetic stimulation electroencephalogram data. As used herein, a "generative model" may be a model for generating all values of a phenomenon including, for example, electroencephalogram data associated with transcranial magnetic stimulation.

$$X = BY \tag{1}$$

wherein X may be a matrix of transcranial magnetic stimulation electroencephalogram data that includes a C quantity of rows corresponding to a C quantity of channels and a T quantity of columns corresponding to a T quantity of time points, B may be a mixing matrix with a C quantity of rows corresponding to the C quantity of channels and a K quantity of columns corresponding to a K quantity of independent components, and Y may be a matrix of the component signal having a K quantity of rows corresponding to the K quantity of independent components and a T quantity of columns corresponding to the T quantity of time points.

Referring again to Equation (1), the matrix X may be known while both the matrix B and the matrix Y are unknown. The independent component analysis may be performed in order to estimate Y based on X and an assumption that the time courses of the independent components are statistically independent from each other. In order to address the scaling ambiguity associated with the independent component analysis (i.e., a scaling of the columns of the matrix B may be offset by applying an inverse scaling of the corresponding rows of the matrix Y), each column of the estimated matrix B may be normalized to have unit variance.

Alternately and/or additionally, the preprocessing of the transcranial magnetic stimulation electroencephalogram data may include filtering the transcranial magnetic stimulation electroencephalogram data to remove spectrally irrelevant artifacts. Spectrally irrelevant artifacts may include artifacts with frequencies outside of useful band for transcranial magnetic stimulation electroencephalogram data (e.g., between 8 Hertz and 12 Hertz)). For instance, the transcranial magnetic stimulation electroencephalogram data processor 135A may apply a high-pass filter (e.g., a 0.01 Hz zero-phase finite impulse response (FIR) filter) to remove excessively low frequency transcranial magnetic stimulation electroencephalogram data. Low frequency transcranial magnetic stimulation electroencephalogram data may typically arise from slow drifts caused by a change in the electric potential across the subject's skin, which may be triggered by the activation of sweat glands due to sympathetic nerve activities. The transcranial magnetic stimulation electroencephalogram data processor 135A may also apply a multi-taper regression technique to identify, via a Thompson F-statistic, excessively high frequency transcranial magnetic stimulation electroencephalogram data, which is typically a product of 60 Hertz alternating current (AC) line noise. It should be appreciated that the transcranial magnetic stimulation electroencephalogram data processor 135A may apply different filtering techniques to remove spectrally irrelevant transcranial magnetic stimulation electroencephalogram data.

In some example embodiments, the preprocessing of transcranial magnetic stimulation electroencephalogram data may further include epoching the filtered transcranial magnetic stimulation electroencephalogram data with respect to the transcranial magnetic stimuli. That is, the filtered transcranial magnetic stimulation electroencephalogram data, which may initially be continuous, may be divided into epochs corresponding to the trials of transcranial magnetic stimuli that are administered to the subject. Thus, a single transcranial magnetic stimulation epoch may be a segment of transcranial magnetic stimulation electroencephalogram data that corresponds to the subject's response to a single transcranial magnetic stimulus, a pair of transcranial magnetic stimuli, and/or a train of transcranial magnetic stimuli. The segment of transcranial magnetic stimulation electroencephalogram data may span 500 to 1500 milliseconds and/or a different quantity of time.

Alternately and/or additionally, the transcranial magnetic stimulation electroencephalogram data processor 135A may preprocess the filtered transcranial magnetic stimulation electroencephalogram data by re-referencing the filtered transcranial magnetic stimulation electroencephalogram data with respect to a common average. As noted earlier, the electroencephalogram device 120 may record transcranial magnetic stimulation electroencephalogram data by at least measuring voltage differentials with respect to a reference electrode (e.g., the first electrode 122). The re-referencing of the transcranial magnetic stimulation electroencephalogram data may include re-referencing the transcranial magnetic stimulation electroencephalogram data with respect to a common average of activities across all recording electrodes (e.g., the second electrode 124 and the third electrode 126). For example, the average voltage differential across all recording electrodes may be subtracted from the voltage differential at each individual recording electrode.

In some example embodiments, the transcranial magnetic stimulation electroencephalogram data processor 135A may identify and remove artifacts associated with one or more bad epochs and/or bad electrodes. As noted, a single epoch may be a 500 to 1500 millisecond segment of transcranial magnetic stimulation electroencephalogram data that corresponds to the subject's response to a single transcranial magnetic stimulus, a pair of transcranial magnetic stimuli, and/or a train of transcranial magnetic stimuli. Meanwhile, a bad epoch may refer to an epoch that is contaminated with artifacts arising from subject motion including, for example, head movement, scalp scratch, jaw clench, talking, swallowing, throat clearing, and/or the like. Such motion artifacts may be spatially widespread and may contaminate all channels in an epoch. Moreover, motion artifacts may introduce nonlinearities into the transcranial magnetic stimulation electroencephalogram data, thereby increasing the quantity of independent components for capturing the variability of artefactual contributions while reducing the quantity of available independent components for separating neural and artefactual sources. As such, motion artifacts may be pruned from the transcranial magnetic stimulation electroencephalogram data prior to the identification and rejection of artefactual independent components.

To identify and remove artifacts from bad epochs, the transcranial magnetic stimulation electroencephalogram data processor 135A may determine a z-score for the magnitude of various combinations of epochs n and channel c as set forth in Equation (2) below.

$$z_{n,c} = \frac{a_{n,c} - m_c}{s_c} \tag{2}$$

wherein $a_{n,c}$ may correspond to an average magnitude of the n-th epoch and the c-th channel, $m_c$ may correspond to a mean of the average magnitude across epochs for the c-th channel, and $s_c$ may correspond to a standard deviation of the average magnitude across epochs for the c-th channel. It should be appreciated that electroencephalogram data recorded up to a certain quantity of time (e.g., 50 milliseconds) subsequent to the administration of transcranial magnetic stimulation may be omitted from the determination of the z-score in order to decrease inference from any residual decay artifacts.

The transcranial magnetic stimulation electroencephalogram data processor 135A may identify combinations of epochs and channels having a z-score that exceeds a threshold value (e.g., 3). From those combinations that are identified, epochs that appear in more than a threshold proportion (e.g., 20%) of all channels may be rejected across all channels. Meanwhile, epochs that appear in fewer than the threshold proportion of channels, the electroencephalogram values in the corresponding channels may be replaced based on an interpolation (e.g., spherical interpolation) of electroencephalogram values from adjacent channels. For transcranial magnetic stimulation electroencephalogram data having a disproportionately large quantity of bad epochs, artifact elimination based on z-score may reject an undesirably low quantity of epochs because the average magnitude and the standard deviation may both be high. As such, where the proportion of bad epochs is high including, for example, when both the average magnitude and the standard deviation are high, the transcranial magnetic stimulation electroencephalogram data processor 135A may provide a warning, which may show the channels in which the standard deviation of the average magnitude across epochs exceeds a threshold value (e.g., 30 microvolts).

As noted, the transcranial magnetic stimulation electroencephalogram data processor 135A may also remove artifacts from bad electrodes. For example, the transcranial magnetic stimulation electroencephalogram data processor 135A may identify one or more bad electrodes in the electroencephalogram device 120 and remove a portion of the electroencephalogram data recorded by these bad electrodes. Furthermore, the transcranial magnetic stimulation electroencephalogram data processor 135A may replace the electroencephalogram data recorded by bad electrodes with data recorded by adjacent electrodes. For instance, the electroencephalogram data recorded by a bad electrode may be replaced by an interpolation (e.g., spherical interpolation) of the electroencephalogram data recorded by its neighboring electrodes. As used herein, a "bad electrode" may refer to an electrode that produces abnormal electroencephalogram data due to, for example, being faulty, disconnected, and/or flat. The electroencephalogram data of the electrode may be abnormal if it deviates from the electroencephalogram data recorded by neighboring electrodes and/or a random sampling of electrodes in the electroencephalogram device 120.

In some example embodiments, to identify bad electrodes, the transcranial magnetic stimulation electroencephalogram data processor 135A may determine, for each epoch, a maximum correlation efficient of the electroencephalogram data from each electrode in the electroencephalogram device 120 relative to the rest of the electrodes in the electroencephalogram device 120. The maximum correlation efficient may be a measure of the deviation in the electroencephalogram data recorded by an electrode relative to the electroencephalogram data recorded by other (e.g., neighboring) electrodes in the electroencephalogram device 120. Here, electroencephalogram data recorded up to a certain quantity of time (e.g., 50 milliseconds) subsequent to the administration of transcranial magnetic stimulation may also be omitted from the determination of the maximum correlation efficient. Moreover, an electrode may be identified as a bad electrode if its maximum correlation efficient is less than a threshold value (e.g., 0.5) for more than a threshold proportion (e.g., 5%) of epochs.

It should be appreciated that the identification of bad electrodes may be affected by the choice of reference. When a single inactive electrode is used as the reference electrode, the electrode should ideally be as noise-free as possible because referencing a noisy electrode may inflate the correlation coefficient between the electroencephalograms data recorded at different electrodes. Nevertheless, a single reference electrode may be skewed by an extreme outlier electrode. As such, in some example embodiments, the identification of bad electrodes may be performed iteratively along with the determination of a common average reference. Table 1 below depicts an algorithm for iteratively identifying bad electrodes and determining a common average reference.

TABLE 1

1. Initialize EEG to electroencephalogram data and bad electrode list to an empty array [ ].
2. $EEG_{temp}$ = EEG − median(EEG), wherein median(EEG) may be the median of the electroencephalogram data across all of the electrodes in the electroencephalogram device 120;
3. Identify one or more bad electrodes from $EEG_{temp}$ based on the maximum correlation coefficient and add the bad electrode to the bad electrode list;
4. $EEG_{temp}$ = EEG − median($EEG_{interp}$), wherein $EEG_{interp}$ may be the mean of the electroencephalogram data with electroencephalogram data recorded by the bad electrodes in the bad electrode list interpolated;
5. Repeat operations 2-3 until the bad electrode list does not change.
6. Reject and interpolate the electroencephalogram data recorded by the bad electrodes in the bad electrode list;
7. Update the electroencephalogram data such that EEG = EEG − median(EEG)

The maximum correlation coefficient may be capable of identifying only single noisy electrodes but not a cluster of bad electrodes. This may be due to the cluster of bad electrodes exhibiting a high degree of correlation amongst themselves. As such, in some example embodiments, a random consensus technique (RANSAC) may be used to identify clusters of bad electrodes in addition to and/or instead of the maximum correlation coefficient. For example, the random consensus technique may determine, based on the electroencephalogram data recorded by a random subset (e.g., 25%) of electrodes in the electroencephalogram device 120, a prediction of the electroencephalogram data that should be recorded by the other electrodes (e.g., exclusive of the subset) in each epoch. The transcranial magnetic stimulation electroencephalogram data processor 135A may repeat this prediction multiple times (e.g., 50 times). Moreover, the transcranial magnetic stimulation electroencephalogram data processor 135A may determine correlation coefficients between the predicted electroencephalogram data and the actual electroencephalogram data recorded at each electrode in the electroencephalogram device 120 (e.g., exclusive of the subset). An electrode may be identified as a bad electrode if, for example, the median (e.g., 50 percentile) of that electrode's correlation coefficient is less than a threshold value (e.g., 0.75) on more than a certain proportion of epochs (e.g., 0.4).

The transcranial magnetic stimulation electroencephalogram data processor 135A may perform artifact rejection by at least decomposing the preprocessed transcranial magnetic stimulation electroencephalogram data into a plurality of independent components. In some example embodiment, the transcranial magnetic stimulation electroencephalogram data processor 135A may perform artifact rejection by applying a machine learning model that is trained to identify one or more artefactual independent components. The machine learning model may be a classifier including, for example, a Fisher linear discriminant analyzer although different and/or additional types of machine learning models (e.g., a neural network) may also be applied in order to perform artifact rejection. Artefactual independent components may be removed from the transcranial magnetic stimulation electroencephalogram data used to perform real-time adjustments to the parameters of a transcranial magnetic stimulation procedure (e.g., administered by the transcranial magnetic stimulation device 110).

The transcranial magnetic stimulation electroencephalogram data processor 135A may generate a feature vector $\mathbb{V}$ for each independent component i, which may be associated with a corresponding scalp map $s_i$ and a time course $y_i$. The feature vector $\mathbb{V}$ may include an n quantity of features $[f_1, f_2, \ldots, f_n]$ that capture the spatial, temporal, and/or spectral patterns that are present in the corresponding independent component. According to some example embodiments, the transcranial magnetic stimulation electroencephalogram data processor 135A may apply, to the feature vector $\mathbb{V}$, a Fisher linear discriminant analyzer and/or the like. The Fisher linear discriminant analyzer may be trained to determine a linear combination of the features $[f_1, f_2, \ldots, f_n]$ that distinguishes between artefactual and non-artefactual independent components. The Fisher linear discriminant analyzer may be trained based on training data that includes electroencephalogram data associated with transcranial magnetic stimulation. The electroencephalogram data used for training may include one or more independent components having known classifications (e.g., as an artefactual independent component and/or a non-artefactual independent component).

Training the Fisher linear discriminant analyzer may include adjusting the weight that is associated with each feature $[f_1, f_2, \ldots, f_n]$ until the Fisher linear discriminant analyzer is able to determine the correct classification for the independent components in the training data. For example, the weights may be adjusted in order to maximize a ratio of inter-class (e.g., between class) variance and intra-class (e.g., within class) variance. Here, a class may refer to a group of same and/or similar independent components. For instance, artefactual independent components may form one class while non-artefactual independent components may form another class. Accordingly, the weights may be adjusted in order to maximize the inter-class variation between artefactual and non-artefactual components while minimizing the intra-class variation amongst artefactual independent components and the intra-class variation amongst non-artefactual independent components.

In some example embodiments, the feature vector may include a plurality of features including, for example, spatial range, regional activation, border activation, correlation with horizontal eye movement template, correlation with blink artifact template, electrocardiogram (EKG) spatial correlation, electrocardiogram temporal correlation, current source density, maximum magnitude, short-time magnitude, skewness, band-power for electroencephalogram rhythms, and electroencephalogram spectrum.

The spatial range feature of an independent component i may correspond to an absolute difference between a maximum voltage differential and a minimum voltage differential present in the corresponding scalp map $s_i$. It should be appreciated that an artefactual independent component is typically associated with a large spatial range.

The regional activation feature of an independent component i may correspond to an absolute value of the average voltage differentials recorded within one or more specific regions (e.g., central, frontal, occipital, and/or temporal) of the corresponding scalp map $s_i$.

The border activation feature of an independent component i may be a value (e.g., a "1" or a "0") indicative of whether the electrode recording the highest voltage differential in the corresponding scalp map $s_i$ is located on the border of the scalp map $s_i$. In should be appreciated that the highest voltage differential recorded for a non-artefactual independent component generally may not located at the border of the corresponding scalp map.

In some example embodiments, the scalp map $s_i$ of an independent component i may be compared to a template scalp map showing a spatial distribution of voltage differentials that may result from horizontal eye movement. FIG. 3A depicts a template scalp map 300 that shows the spatial distribution of electrodes that are activated by a subject's horizontal eye movement as well as the magnitude of the voltage differential recorded at each electrode. The transcranial magnetic stimulation electroencephalogram data processor 135A may compare the scalp map $s_i$ of an independent component i and the template scalp map 300 to determine an absolute correlation coefficient between the scalp map $s_i$ and the template scalp map 300. The correlation with horizontal eye movement template feature of the feature vector $\mathbb{V}$ may be this absolute correlation coefficient indicative of a degree of correspondence between the scalp map $s_i$ of the independent component i and the template scalp map 300 for horizontal eye movement.

In some example embodiments, the scalp map $s_i$ of an independent component i may be compared to a template scalp map showing a spatial distribution of voltage differentials that may result from transcranial magnetic stimulation-evoked and/or voluntary eye blinking movements. FIG. 3B depicts a template scalp map 310 illustrating the spatial distribution of electrodes that are activated by a subject's blinking movements. As shown in FIG. 3B, the subject's blinking movements tend to trigger a high degree of activation and large voltage differentials in the electrodes located in the prefrontal region of the template scalp map 310. The transcranial magnetic stimulation electroencephalogram data processor 135A may compare the scalp map $s_i$ of an independent component i and the template scalp map 310 to determine an absolute correlation coefficient between the scalp map $s_i$ and the template scalp map 310. The correlation with blink template feature of the feature vector $\mathbb{V}$ may be this absolute correlation coefficient indicative of a degree of correspondence between the scalp map $s_i$ of the independent component i and the template scalp map 310 for blinking movements.

In some example embodiments, an electrocardiogram artifact may be a poorly formed QRS complex that is time-locked to a subject's cardiac contractions. This electrocardiogram artifact may be most prominent when the subject's neck is short and wide. According to some example embodiments, the scalp map $s_i$ of an independent component i may be compared to one or more template scalp maps showing a spatial distribution of voltage differentials that correspond to an electrocardiogram artifact. FIG. 3C depicts a collection of template scalp maps 320 that show the various spatial distribution of electrodes that can activated due to a subject's cardiac contractions. As shown in FIG. 3C, the subject's cardiac contracts may to activate electrodes at different locations. Thus, the transcranial magnetic stimulation electroencephalogram data processor 135A may compare the scalp map $s_i$ of an independent component i and the each of the template scalp maps in the collection of template scalp maps 320 to determine an absolute correlation coefficient between the scalp map $s_i$ and each of the template scalp maps in the collection. The electrocardiogram spatial correlation feature of the feature vector may be a value (e.g., a "1" or "0") indicating whether the maximum correlation coefficient between the scalp map $s_i$ and the template scalp maps exceeds a threshold value (e.g., 0.5).

In some example embodiments, the transcranial magnetic stimulation electroencephalogram data processor 135A may be configured to detect the occurrence of electrocardiogram artifacts during the time course $y_i$ of the independent component i. It should be appreciated that the electrocardiogram artifact may have a certain duration (e.g., approximately 50 ms) and/or frequency (e.g., between 1 Hertz and 1.67 Hertz). Accordingly, the transcranial magnetic stimulation electroencephalogram data processor 135A may detect the QRS complex associated with the electrocardiogram artifact by at least applying a maximal overlap discrete wavelet transform (MODWT). By applying a wavelet that resembles the QRS complex in shape, a higher specificity of an independent component that is an electrocardiogram artifact may be achieved. For instance, the transcranial magnetic stimulation electroencephalogram data processor 135A may be able to detect peaks at an appropriate scale in the wavelet subspace rather than in the original signal space. Specifically, to detect electrocardiogram artifacts, the transcranial magnetic stimulation electroencephalogram data processor 135A may be configured to decompose the time course $y_i$ of the independent component i using the Daubechies least-asymmetric wavelet with 4 vanishing moments ('sym4') wavelet. The depth of the decomposition, M may be determined based on the following Equation (3):

$$\frac{F_s}{2^{M+1}} < 50 < \frac{F_s}{2^M} \quad (3)$$

wherein $F_s$ is the sampling rate of the electroencephalogram data.

The transcranial magnetic stimulation electroencephalogram data processor 135A may reconstruct a signal $z_i$ using the wavelet coefficients at scale M+1, which corresponds to the following Equation (4):

$$\frac{F_s}{2^{M+1}} - \frac{F_s}{2^M} \text{ Hertz} \quad (4)$$

Figure 3D:
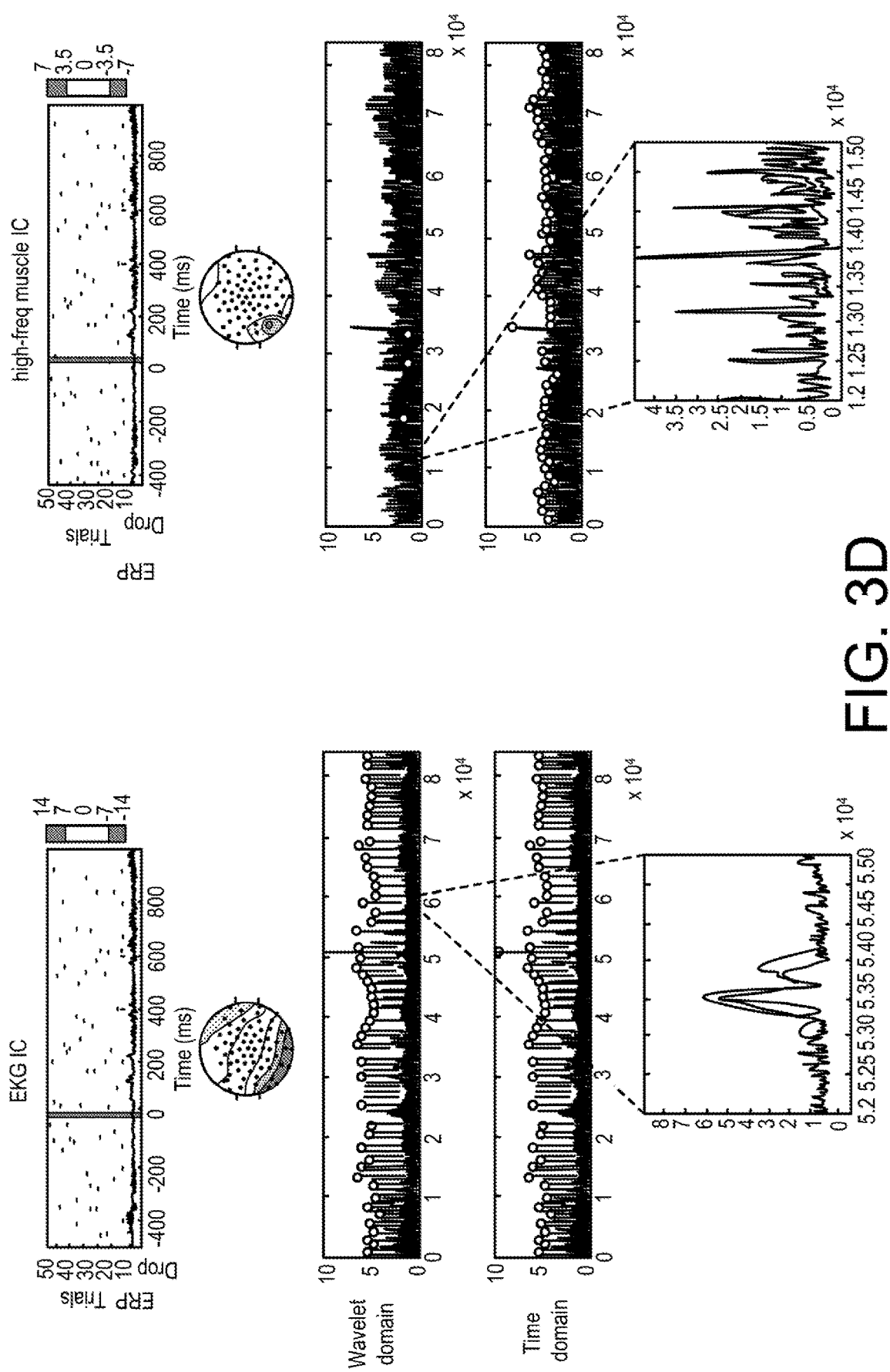
FIG. 3D depicts results from peak detection in the wavelet domain and the time domain, in accordance with some example embodiments.

The transcranial magnetic stimulation electroencephalogram data processor 135A may identify the number of peaks in $z_i^2$ $z_i^2$. Here, the minimum inter peak distance may be set to 600 millisecond to match the frequency of the electrocardiogram artifact. The electrocardiogram temporal feature of the feature vector $\mathbb{V}$ may be a value (e.g., a "0" or "1") that indicates whether the number of peaks is greater than a threshold value. The threshold value may be 0.8NT, wherein N may be a total number of trials and T be a length of each epoched trial in seconds. FIG. 3D depicts the results of peak detection in the wavelet domain and the time domain. It should be appreciated that peak detection in the wavelet domain may be less susceptible to false positives than peak detection in the time domain.

Artefactual independent components may be associated with sources having complicated patterns and large $l_2$ norms. The source activity s may be estimated using a minimum norm estimation technique on a boundary element head model built from the average structural magnetic resonance images (MRIs) of a group of subjects. The current source density feature of the feature vector $\mathbb{V}$ may correspond to the $l_2$ norm of the estimated source activity s. As used herein, the source activity s may originate from a cortical source. The $l_2$ norm of the estimated source activity s may correspond to a spatial map of each source.

In some example embodiments, the maximum magnitude feature of the feature vector $\mathbb{V}$ may correspond to the maximum voltage differential that is recorded across trials over the duration of a transcranial magnetic stimulation procedure or session.

In some example embodiments, the transcranial magnetic stimulation electroencephalogram data processor 135A may determine the mean magnitudes of different time windows in order to capture various transcranial magnetic stimulation-evoked potential (TEP) peaks and transcranial magnetic stimulation-evoked muscle artifacts. For example, the short-time magnitude feature of the feature vector $\mathbb{V}$ may include the mean magnitudes for a 0-60 millisecond time window, a 60-120 millisecond time window, and/or a 140-220 millisecond time window. The length of these time windows may be adjusted to capture transcranial magnetic stimulation-evoked potential peaks that may be present when different regions of the brain are stimulated and/or capture artifacts that are time-locked to the transcranial magnetic stimuli administered to the subject. It should be appreciated that the computation of mean magnitudes for relatively broad time-frames may enable a quantification of transcranial magnetic stimulation-evoked potential peaks without allowing for spurious fluctuations. Thus, the transcranial magnetic stimulation electroencephalogram data processor 135A may be able to capture transcranial magnetic stimulation-evoked potential peaks that are significantly earlier and/or later than typical transcranial magnetic stimulation peaks due to variability amongst different subjects.

In some example embodiments, the skewness associated with an independent component i may be a measure of the asymmetry in the probability distribution in the corresponding transcranial magnetic stimulation electroencephalogram data. The skewness feature of the feature vector $\mathbb{V}$ may be the absolute value of the mean skewness across all of the trials that are conducted during a transcranial magnetic stimulation procedure or session.

In some example embodiments, the transcranial magnetic stimulation electroencephalogram data processor 135A may capture various electroencephalogram rhythms by at least computing the band-power for one or more electroencephalogram bands including, for example, the theta band (e.g., the 4-7 Hertz band), the alpha band (e.g., the 8-12 Hertz band), the beta band (e.g., the 13-30 Hertz band), and/or the gamma band (e.g., the 31-50 Hertz band). Thus, the band-power feature of the feature may include the band-power for the theta band, the alpha band, the beta band, and/or the gamma band. It should be appreciated that the gamma band-power may enable a detection of high-frequency muscle artifacts.

In some example embodiments, the transcranial magnetic stimulation electroencephalogram data processor 135A may determine one or more electroencephalogram spectral features, which may be included in the feature vector $\mathbb{V}$. Except for the alpha band, typical electroencephalogram spectrum may follow a $$\frac{1}{f}$$

shape, wherein f may refer to the frequencies of the spectrum. Thus, in order to extract the electroencephalogram spectral features, the transcranial magnetic stimulation electroencephalogram data processor 115 may fit the spectrum of an independent component i that is between 1 Hertz and 35 Hertz to the following Equation (5):

$$y = \frac{a}{f^b} + c(b > 0) \qquad (5)$$

Figure 3E:
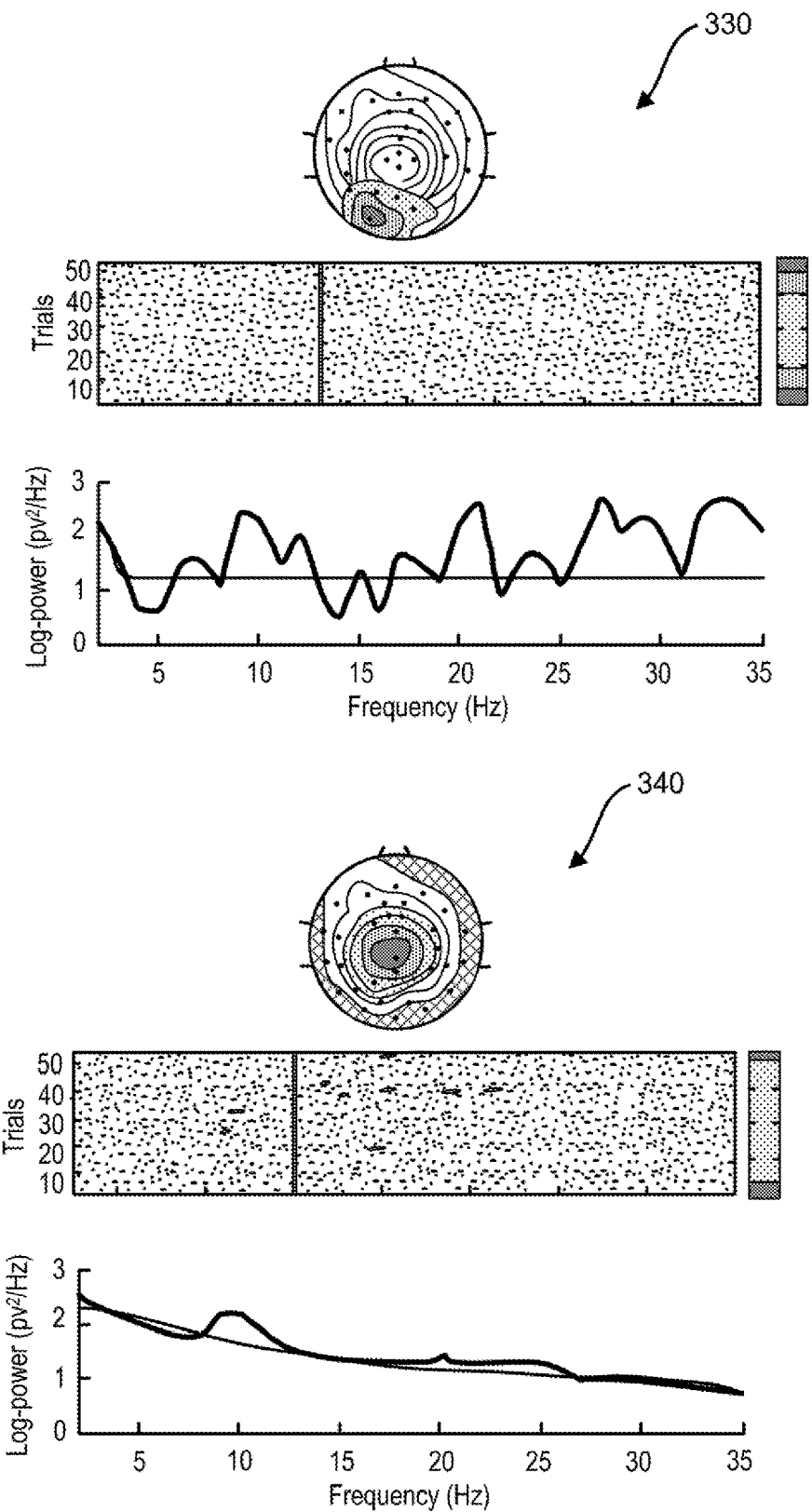
FIG. 3E depicts spectral features associated with transcranial magnetic stimulation electroencephalogram data, in accordance with some example embodiments.

The transcranial magnetic stimulation electroencephalogram data processor 135A may then extract a first spectral feature that corresponds to the mean fit error between the actual spectrum of the independent component i and the fitted $$\frac{1}{f}$$

within the alpha band. The transcranial magnetic stimulation electroencephalogram data processor 135A may further extract a second spectral feature that corresponds to the parameter b from the above Equation (5). It should be appreciated that artefactual independent components typically have a higher value for the parameter b than non-artefactual independent components. FIG. 3E depicts spectral features 330 for an independent component that is associated with artefactual source (e.g., muscle movement) and spectral features 340 for an independent component that is associated with a non-artefactual source. Referring to FIG. 3E, the artefactual source may be associated with an alpha-band fit error of 1.23 and $\lambda=1.74$ while the non-artefactual source may be associated with an alpha-band fit error of 4.35 and $\lambda=-4.83$.

Figure 4A:
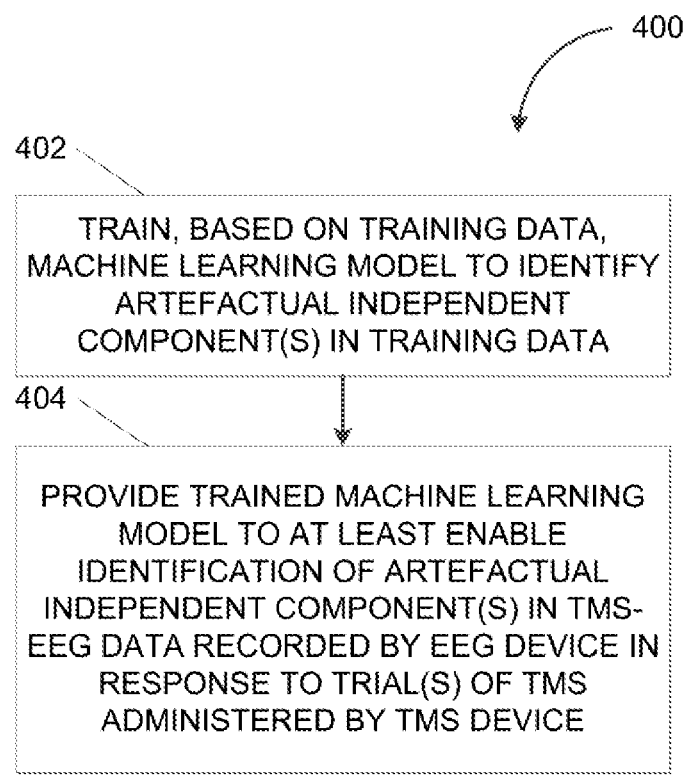
FIG. 4A depicts a flowchart illustrating a process for training a machine learning model to perform artifact rejection, in accordance with some example embodiments.

FIG. 4A depicts a flowchart illustrating a process 400 for training a machine learning model to perform artifact rejection, in accordance with some example embodiments. Referring to FIGS. 1-4A, the process 400 may be performed by the controller 130, for example, by the machine learning engine 135B.

The controller 130 may train, based on training data, a machine learning model to identify one or more artefactual independent components in the training data (402). In some example embodiments, the machine learning model may be trained with training data that includes electroencephalogram data associated with transcranial magnetic stimulation. This electroencephalogram data may be include one or more independent components with known classifications including, for example, independent components that are known to be artefactual and/or non-artefactual. It should be appreciated that the artefactual independent components may originate from a variety of sources including, for example, transcranial magnetic stimuli, subject motion (e.g., scalp muscle activation, eye blinks), coil clicks, coil recharge, and/or the like.

In some example embodiments, the machine learning model may be trained to determine a linear combination of the features that distinguishes between artefactual and non-artefactual independent components. Training the machine learning model may include adjusting the weight that is associated with each feature until the machine learning model is able to determine the correct classification for the independent components in the training data. For example, the weights may be adjusted in order to maximize the inter-class variation between artefactual and non-artefactual components while minimizing the intra-class variation amongst artefactual independent components and the intra-class variation amongst non-artefactual independent components.

The controller 130 may provide the trained machine learning model to at least enable an identification of one or more artefactual independent components in the electroencephalogram data recorded by the electroencephalogram device 120 in response to one or more trials of transcranial magnetic stimuli administered by the transcranial magnetic stimulation device 110 (404). In some example embodiments, the trained machine learning model may be trained by the machine learning engine 135B and deployed locally at the controller 130. However, it should be appreciated that the training of the machine learning model may be performed at a remote computing system and the trained machine learning model may be deployed as computer software that is delivered to the controller 130, for example, via the network 140.

Figure 4B:
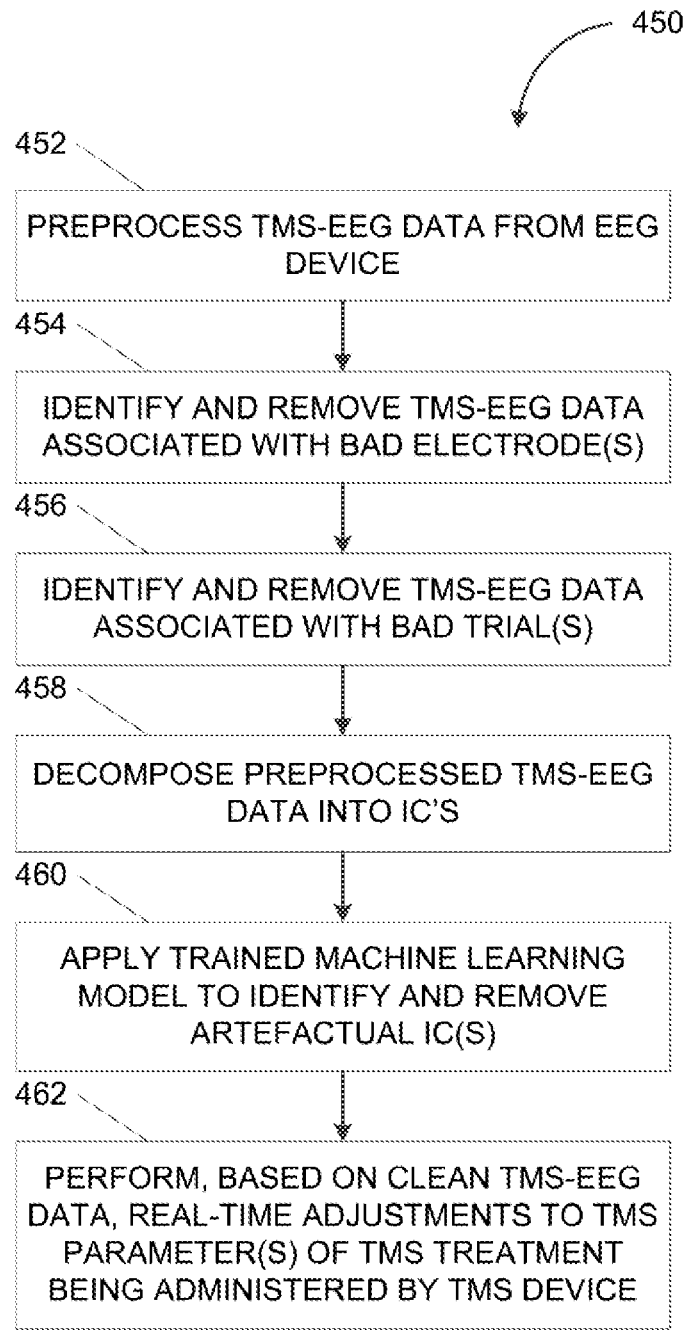
FIG. 4B depicts a flowchart illustrating a process for artifact rejection, in accordance with some example embodiments.

FIG. 4B depicts a flowchart illustrating a process 450 for artifact rejection, in accordance with some example embodiments. Referring to FIGS. 1-4B, the process 450 may be performed by the controller 130, for example, by the transcranial magnetic stimulation electroencephalogram data processor 135A.

In some example embodiments, the controller 130 may preprocess transcranial magnetic stimulation electroencephalogram data received from the electroencephalogram device 120 (452). For instance, the controller 130 (e.g., the transcranial magnetic stimulation electroencephalogram data processor 135A) may preprocess the transcranial magnetic stimulation electroencephalogram data by at least removing artifacts associated with the transcranial magnetic stimuli (e.g., the first 10 milliseconds of the transcranial magnetic stimulation electroencephalogram data subsequent to the administration of one or more transcranial magnetic stimuli) and/or spectrally irrelevant artifacts (e.g., excessively high frequency transcranial magnetic stimulation electroencephalogram data caused by AC line noise and/or low frequency transcranial magnetic stimulation electroencephalogram data caused by slow drifts). The preprocessing of the transcranial magnetic stimulation electroencephalogram data may further include epoching the transcranial magnetic stimulation electroencephalogram data and/or re-referencing the transcranial magnetic stimulation electroencephalogram data to a common average.

The controller 130 may identify and remove transcranial magnetic stimulation electroencephalogram data associated with one or more bad electrodes (454). For example, the controller 130 (e.g., the transcranial magnetic stimulation electroencephalogram data processor 135A) may identify one or more bad electrodes recording abnormal electroencephalogram data due to being faulty, disconnected, and/or flat. As noted, the electroencephalogram data of an electrode may be abnormal if it deviates from the electroencephalogram data recorded by neighboring electrodes and/or a random sampling of electrodes in the electroencephalogram device 120. In some example embodiments, the controller 130 may identify bad electrodes based on the maximum correlation efficient of the electroencephalogram data from each electrode in the electroencephalogram device 120 relative to the electroencephalogram data recorded by neighboring electrodes in the electroencephalogram device 120. Alternatively and/or additionally, the controller 130 may identify bad electrodes based on the correlation coefficient of the electroencephalogram data from the electrodes in the electroencephalogram device 120 relative to the electroencephalogram data recorded by a random sampling of electrodes in the electroencephalogram device 120.

The controller 130 may identify and remove transcranial magnetic stimulation electroencephalogram data associated with one or more bad trials (456). For instance, the controller 130 (e.g., the transcranial magnetic stimulation electroencephalogram data processor 135A) may be configured to remove the transcranial magnetic stimulation electroencephalogram data associated with a particular transcranial magnetic stimulation trial, when the magnitude of the voltage differential recorded for that transcranial magnetic stimulation trial exceeds the mean magnitude of the voltage differentials recorded for all transcranial magnetic stimulation trials during a transcranial magnetic stimulation procedure by a certain number (e.g., three) of standard deviations.

The controller 130 may decompose the preprocessed transcranial magnetic stimulation electroencephalogram data into a plurality of independent components (458). For instance, the controller 130 (e.g., the transcranial magnetic stimulation electroencephalogram data processor 135A may decompose the transcranial magnetic stimulation electroencephalogram data into a plurality of independent components, which may originate from artefactual or non-artefactual sources.

The controller 130 may apply a machine learning model to identify and remove one or more artefactual independent components (460). For example, the controller 130 (e.g., the transcranial magnetic stimulation electroencephalogram data processor 135A) may generate, for an independent component, a feature vector $\mathbb{V}$ that includes a plurality of features that capture the spatial, temporal, and/or spectral patterns present in the independent component. The plurality of features may include, for example, spatial range, regional activation, border activation, correlation with horizontal eye movement template, correlation with blink artifact template, electrocardiogram spatial correlation, electrocardiogram temporal correlation, current source density, maximum magnitude, short-time magnitude, skewness, band-power for electroencephalogram rhythms, and electroencephalogram spectrum. The controller 130 may apply, to the feature vector $\mathbb{V}$, a machine learning model including, for example, a Fisher linear discriminant analyzer and/or the like. The Fisher linear discriminant analyzer may be trained to classify, based on the feature vector $\mathbb{V}$, the corresponding independent component as either an artefactual independent component or a non-artefactual independent component. The controller 130 may be configured to remove, from the transcranial magnetic stimulation electroencephalogram data, one or more independent components that have been identified as an artefactual independent component.

The controller 130 may perform, based on the resulting clean transcranial magnetic stimulation electroencephalogram data, real-time adjustments to one or more transcranial magnetic stimulation parameters of a transcranial magnetic stimulation procedure being administered by the transcranial magnetic stimulation device 110 (462). For example, the controller 130 may perform, based on the resulting clean transcranial magnetic stimulation electroencephalogram data, real-time adjustments to one or more transcranial magnetic stimulation parameters including, for example, stimulation duration, stimulation frequency, stimulation magnitude, stimulation area, time interval between stimuli, and/or the like.

FIG. 5A-D depicts transcranial magnetic stimulation electroencephalogram data that has been subject to machine learning based artifact rejection, in accordance with some example embodiments. FIG. 5A depicts the transcranial magnetic stimulation-evoked potential peaks that are found in transcranial magnetic stimulation electroencephalogram data prior to artifact rejection. FIG. 5B depicts the transcranial magnetic stimulation-evoked potential peaks that are found in the transcranial magnetic stimulation electroencephalogram data subsequent to the removal of transcranial magnetic stimulation electroencephalogram data from one or more bad channels. FIG. 5C depicts the transcranial magnetic stimulation-evoked potential peaks that are found in the transcranial magnetic stimulation electroencephalogram data subsequent to the removal of transcranial magnetic stimulation electroencephalogram data from one or more bad trials. FIG. 5D depicts the transcranial magnetic stimulation-evoked potential peaks that are found in the transcranial magnetic stimulation electroencephalogram data subsequent to the removal of one or more artefactual independent components.

Figure 6A:
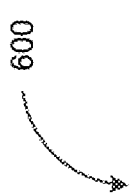
FIG. 6A depicts a table illustrating the classification accuracies, in accordance with some example embodiments.

FIG. 6A depicts a table 600 illustrating classification accuracies for each subject A-F in a leave-one-subject-out classification. As shown in FIG. 6A, machine learning based artifact rejection (e.g., ARTIST) has a higher classification accuracy than manual artifact rejection (e.g., MARA).

FIG. 6B depicts tables 650 illustrating classification accuracies for each site in a leave-one-site-out classification. As shown in FIG. 6B, machine learning based artifact rejection (e.g., ARTIST) has a higher classification accuracy than manual artifact rejection (e.g., MARA).

Figure 7:
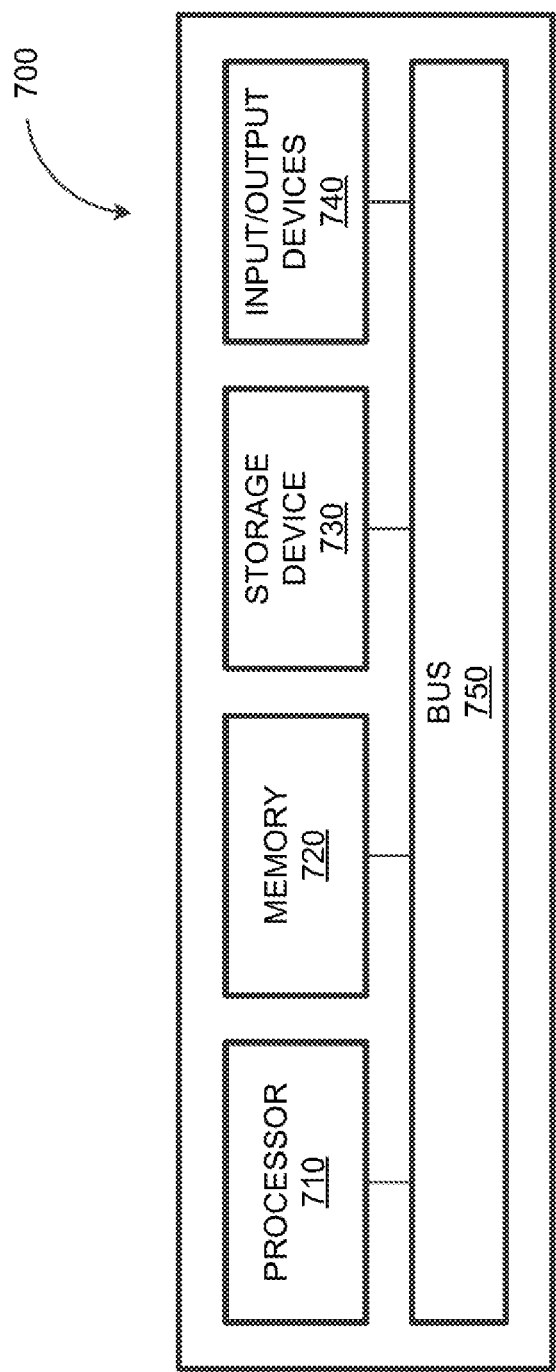
FIG. 7 depicts a block diagram illustrating a computing system, in accordance with some example embodiments.

FIG. 7 depicts a block diagram illustrating a computing system 700 consistent with some implementations of the current subject matter. Referring to FIGS. 1 and 7, the computing system 700 can be used to implement the controller 130 and/or any components therein.

As shown in FIG. 7, the computing system 700 can include a processor 710, a memory 720, a storage device 730, and input/output devices 740. The processor 710, the memory 720, the storage device 730, and the input/output devices 740 can be interconnected via a system bus 750. The processor 710 is capable of processing instructions for execution within the computing system 700. Such executed instructions can implement one or more components of, for example, the controller 130. In some implementations of the current subject matter, the processor 710 can be a single-threaded processor. Alternately, the processor 710 can be a multi-threaded processor. The processor 710 is capable of processing instructions stored in the memory 720 and/or on the storage device 730 to display graphical information for a user interface provided via the input/output device 740.

The memory 720 is a computer readable medium such as volatile or non-volatile that stores information within the computing system 700. The memory 720 can store data structures representing configuration object databases, for example. The storage device 730 is capable of providing persistent storage for the computing system 700. The storage device 730 can be a floppy disk device, a hard disk device, an optical disk device, or a tape device, or other suitable persistent storage means. The input/output device 740 provides input/output operations for the computing system 700. In some implementations of the current subject matter, the input/output device 740 includes a keyboard and/or pointing device. In various implementations, the input/output device 740 includes a display unit for displaying graphical user interfaces.

According to some implementations of the current subject matter, the input/output device 740 can provide input/output operations for a network device. For example, the input/output device 740 can include Ethernet ports or other networking ports to communicate with one or more wired and/or wireless networks (e.g., a local area network (LAN), a wide area network (WAN), the Internet).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A computer-implemented method, comprising:
   decomposing transcranial magnetic stimulation electroencephalogram data collected during a transcranial magnetic stimulation procedure, the transcranial magnetic stimulation electroencephalogram data comprising a multivariate signal, the transcranial magnetic stimulation electroencephalogram data being decomposed into a plurality of independent components, and each independent component of the plurality of independent components being a non-Gaussian signal forming the multivariate signal;
   applying, to the plurality of independent components, a machine learning model to identify one or more artefactual independent components comprising the transcranial magnetic stimulation electroencephalogram data;
   generating clean transcranial magnetic stimulation electroencephalogram data by at least removing, from the transcranial magnetic stimulation electroencephalogram data, the one or more artefactual independent components; and
   performing, based at least on the clean transcranial magnetic stimulation electroencephalogram data, adjustments to one or more parameters of the transcranial magnetic stimulation procedure.

2. A system, comprising:
   at least one processor; and
   at least one memory including program code which when executed by the at least one processor results in operations comprising:
      decomposing transcranial magnetic stimulation electroencephalogram data collected during a transcranial magnetic stimulation procedure, the transcranial magnetic stimulation electroencephalogram data comprising a multivariate signal, the transcranial magnetic stimulation electroencephalogram data being decomposed into a plurality of independent components, and each independent component of the plurality of independent components being a non-Gaussian signal forming the multivariate signal;

applying, to the plurality of independent components, a machine learning model to identify one or more artefactual independent components comprising the transcranial magnetic stimulation electroencephalogram data;

generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, real-time adjustments to one or more parameters of the transcranial magnetic stimulation procedure.

3. The system of claim 2, wherein the operations further comprise:

preprocessing the transcranial magnetic stimulation electroencephalogram data prior to decomposing the transcranial magnetic simulation electroencephalogram data into the plurality of independent components, wherein the preprocessing includes one or more of
(i) removing a portion of the transcranial magnetic stimulation electroencephalogram data that is recorded within a threshold quantity of time subsequent to administration of one or more transcranial magnetic stimuli,
(ii) filtering the transcranial magnetic stimulation electroencephalogram data to remove spectrally irrelevant artifacts associated with frequencies outside of a useful band between 8 hertz and 12 hertz, and
(iii) epoching the transcranial magnetic stimulation electroencephalogram data and/or re-referencing the transcranial magnetic stimulation electroencephalogram data with respect to a common average.

4. The system of claim 2, wherein the operations further comprise:

generating a feature vector, wherein the feature vector includes one or more independent components of the plurality of independent components comprising the transcranial magnetic stimulation electroencephalogram data.

5. The system of claim 4, wherein the feature vector includes a spatial range feature that includes an absolute difference between a maximum voltage differential and a minimum voltage differential present in a scalp map associated with the one or more independent components.

6. The system of claim 4, wherein the feature vector includes a regional activation feature that includes an absolute value of an average voltage differential recorded within one or more specific regions of a scalp map associated with the one or more independent components, and wherein the one or more specific regions include a central region, a frontal region, an occipital region, and/or temporal region of a brain.

7. The system of claim 4, wherein the feature vector includes a border activation feature that includes whether an electrode recording a highest voltage differential in a scalp map associated with the one or more independent components is located on a border of the scalp map.

8. The system of claim 4, wherein the feature vector includes a horizontal eye movement feature that includes a result of a comparison between a scalp map associated with the one or more independent components and a template scalp map associated with horizontal eye movement, and wherein the result of the comparison comprises an absolute correlation coefficient indicative of a degree of correspondence between the scalp map of the one or more independent components and the template scalp map for horizontal eye movement.

9. The system of claim 4, wherein the feature vector includes an eye blinking feature that includes a result of a comparison between a scalp map associated with the one or more independent components and a template scalp map associated with eye blinking movements, wherein the result of the comparison comprises an absolute correlation coefficient indicative of a degree of correspondence between the scalp map of the one or more independent components and the template scalp map for eye blinking movements, and wherein the eye blinking movement comprises transcranial magnetic stimulation-evoked eye blinking movements and/or voluntary eye blinking movements.

10. The system of claim 4, wherein the feature vector includes an electrocardiogram artifact feature that includes a result of a comparison between a scalp map associated with the one or more independent components and a plurality of template scalp maps associated with cardiac contractions, and wherein the electrocardiogram artifact feature is a value indicating whether a maximum correlation coefficient of the comparison between the scalp map for the one or more independent components and the plurality of template scalp maps exceeds a threshold value.

11. The system of claim 4, wherein the feature vector includes an electrocardiogram temporal feature that includes whether a number of peaks present in the one or more independent components exceeds a threshold value, wherein the one or more independent components are decomposed by at least applying a Daubechies least-asymmetric wavelet, and wherein the one or more independent components are decomposed to enable peak detection to be performed in a wavelet domain instead of a time domain.

12. The system of claim 4, wherein the feature vector includes a source activity feature that includes a complexity of a source pattern associated with the one or more independent components.

13. The system of claim 4, wherein the feature vector includes a maximum magnitude feature that includes a maximum voltage differential that is recorded across a plurality of trials of transcranial magnetic stimuli that are administered during the transcranial magnetic stimulation procedure, and wherein each trial of transcranial magnetic stimuli comprises an administration of a single transcranial magnetic stimulation pulse, a pair of transcranial magnetic stimulation pulses, and/or a train of transcranial magnetic stimulation pulses.

14. The system of claim 4, wherein the feature vector includes a short-time magnitude feature that includes one or more transcranial magnetic stimulation-evoked potential peaks present in the one or more independent components, and wherein the one or more transcranial magnetic stimulation-evoked potential peaks are identified by at least determining a mean magnitude of voltage differentials recorded over a plurality of time windows.

15. The system of claim 4, wherein the feature vector includes a skewness feature that includes a measure of asymmetry in a probability distribution of the transcranial magnetic stimulation electroencephalogram data.

16. The system of claim 4, wherein the feature vector includes a band-power feature that includes a band-power for a theta band between 4 Hertz and 7 Hertz, an alpha band between 8 Hertz and 12 Hertz, a beta band between 13 Hertz and 30 Hertz, and/or a gamma band between 31 Hertz and 50 Hertz.

17. The system of claim 4, wherein the feature vector includes an electroencephalogram spectral feature that includes a mean fit error between an actual spectrum of the one or more independent components and a fitted shape of an electroencephalogram spectrum within an alpha band between 8 Hertz and 12 Hertz.

18. The system of claim 4, wherein the feature vector includes an electroencephalogram spectral feature that includes a value of a parameter b in the following equation:

$$y = \frac{a}{f^b} + c(b > 0).$$

19. A non-transitory computer-readable storage medium including program code, which when executed by at least one data processor, cause operations comprising:
decomposing transcranial magnetic stimulation electroencephalogram data collected during a transcranial magnetic stimulation procedure, the transcranial magnetic stimulation electroencephalogram data comprising a multivariate signal, the transcranial magnetic stimulation electroencephalogram data being decomposed into a plurality of independent components, and each independent component of the plurality of independent components being a non-Gaussian signal forming the multivariate signal;
applying, to the plurality of independent components, a machine learning model to identify one or more artefactual independent components comprising the transcranial magnetic stimulation electroencephalogram data;
generating clean transcranial magnetic stimulation electroencephalogram data by at least removing, from the transcranial magnetic stimulation electroencephalogram data, the one or more artefactual independent components; and
performing, based at least on the clean transcranial magnetic stimulation electroencephalogram data, real-time adjustments to one or more parameters of the transcranial magnetic stimulation procedure.

20. A system, comprising:
at least one processor; and
at least one memory including program code which when executed by the at least one processor results in operations comprising:
generating a feature vector including one or more independent components from transcranial magnetic stimulation electroencephalogram data collected during a transcranial magnetic stimulation procedure;
applying a machine learning model to identify, based at least on the feature vector, one or more artefactual independent components comprising the transcranial magnetic stimulation electroencephalogram data collected during the transcranial magnetic stimulation procedure;
generating clean transcranial magnetic stimulation electroencephalogram data by at least removing, from the transcranial magnetic stimulation electroencephalogram data, the one or more artefactual independent components; and
performing, based at least on the clean transcranial magnetic stimulation electroencephalogram data, real-time adjustments to one or more parameters of the transcranial magnetic stimulation procedure.

21. A system, comprising:
at least one processor; and
at least one memory including program code which when executed by the at least one processor results in operations comprising:
generating a feature vector including one or more independent components from transcranial magnetic stimulation electroencephalogram data collected during a transcranial magnetic stimulation procedure, the feature vector including a spatial range feature that includes an absolute difference between a maximum voltage differential and a minimum voltage differential present in a scalp map associated with the one or more independent components;
applying a machine learning model to identify, based at least on the feature vector, one or more artefactual independent components comprising the transcranial magnetic stimulation electroencephalogram data collected during the transcranial magnetic stimulation procedure; generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, real-time adjustments to one or more parameters of the transcranial magnetic stimulation procedure.

22. A system, comprising:
at least one processor; and
at least one memory including program code which when executed by the at least one processor results in operations comprising:
generating a feature vector including one or more independent components from transcranial magnetic stimulation electroencephalogram data collected during a transcranial magnetic stimulation procedure, the feature vector including a regional activation feature that includes an absolute value of an average voltage differential recorded within one or more specific regions of a scalp map associated with the one or more independent components, and wherein the one or more specific regions include a central region, a frontal region, an occipital region, and/or temporal region of a brain;
applying a machine learning model to identify, based at least on the feature vector, one or more artefactual independent components comprising the transcranial magnetic stimulation electroencephalogram data collected during the transcranial magnetic stimulation procedure;
generating clean transcranial magnetic stimulation electroencephalogram data by at least removing, from the transcranial magnetic stimulation electroencephalogram data, the one or more artefactual independent components; and
performing, based at least on the clean transcranial magnetic stimulation electroencephalogram data, real-time adjustments to one or more parameters of the transcranial magnetic stimulation procedure.

23. A system, comprising:

at least one processor; and at least one memory including program code which when executed by the at least one processor results in operations comprising:

generating a feature vector including one or more independent components from transcranial magnetic stimulation electroencephalogram data collected during a transcranial magnetic stimulation procedure, the feature vector including a border activation feature that includes whether an electrode recording a highest voltage differential in a scalp map associated with the one or more independent component is located on a border of the scalp map;

applying a machine learning model to identify, based at least on the feature vector, one or more artefactual independent components comprising the transcranial magnetic stimulation electroencephalogram data collected during the transcranial magnetic stimulation procedure;

generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, real-time adjustments to one or more parameters of the transcranial magnetic stimulation procedure.

24. A system, comprising:

at least one processor; and at least one memory including program code which when executed by the at least one processor results in operations comprising:

generating a feature vector including one or more independent components from transcranial magnetic stimulation electroencephalogram data collected during a transcranial magnetic stimulation procedure, the feature vector including a horizontal eye movement feature that includes a result of a comparison between a scalp map associated with the one or more independent component and a template scalp map associated with horizontal eye movement, and the result of the comparison including an absolute correlation coefficient indicative of a degree of correspondence between the scalp map of the one or more independent components and the template scalp map for horizontal eye movement;

applying a machine learning model to identify, based at least on the feature vector, one or more artefactual independent components comprising the transcranial magnetic stimulation electroencephalogram data collected during the transcranial magnetic stimulation procedure;

generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, real-time adjustments to one or more parameters of the transcranial magnetic stimulation procedure.

25. A system, comprising:

at least one processor; and at least one memory including program code which when executed by the at least one processor results in operations comprising:

generating a feature vector including one or more independent components from transcranial magnetic stimulation electroencephalogram data collected during a transcranial magnetic stimulation procedure, the feature vector including an eye blinking feature that includes a result of a comparison between a scalp map associated with the one or more independent component and a template scalp map associated with eye blinking movements, the result of the comparison including an absolute correlation coefficient indicative of a degree of correspondence between the scalp map of the one or more independent component and the template scalp map for eye blinking movements, and wherein the eye blinking movement comprises transcranial magnetic stimulation-evoked eye blinking movements and/or voluntary eye blinking movements;

applying a machine learning model to identify, based at least on the feature vector, one or more artefactual independent components comprising the transcranial magnetic stimulation electroencephalogram data collected during the transcranial magnetic stimulation procedure;

generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, real-time adjustments to one or more parameters of the transcranial magnetic stimulation procedure.

26. A system, comprising:

at least one processor; and at least one memory including program code which when executed by the at least one processor results in operations comprising:

generating a feature vector including one or more independent components from transcranial magnetic stimulation electroencephalogram data collected during a transcranial magnetic stimulation procedure, the feature vector including an electrocardiogram artifact feature that includes a result of a comparison between a scalp map associated with the one or more independent components and a plurality of template scalp maps associated with cardiac contractions, the electrocardiogram artifact feature being a value indicating whether a maximum correlation coefficient of the comparison between the scalp map for the one or more independent components and the plurality of template scalp maps exceeds a threshold value;

applying a machine learning model to identify, based at least on the feature vector, one or more artefactual independent components comprising the transcranial magnetic stimulation electroencephalogram data collected during the transcranial magnetic stimulation procedure;

generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, real-time adjustments to one or more parameters of the transcranial magnetic stimulation procedure.

27. A system, comprising:

at least one processor; and at least one memory including program code which when executed by the at least one processor results in operations comprising:

generating a feature vector including one or more independent components from transcranial magnetic stimulation electroencephalogram data collected during a transcranial magnetic stimulation procedure, the feature vector including an electrocardiogram temporal feature that includes whether a number of peaks present in the one or more independent components exceeds a threshold value, wherein the one or more independent components are decomposed by at least applying a Daubechies least-asymmetric wavelet, and wherein the one or more independent components are decomposed to enable peak detection to be performed in a wavelet domain instead of a time domain;

applying a machine learning model to identify, based at least on the feature vector, one or more artefactual independent components comprising the transcranial magnetic stimulation electroencephalogram data collected during the transcranial magnetic stimulation procedure;

generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, real-time adjustments to one or more parameters of the transcranial magnetic stimulation procedure.

28. A system, comprising:

at least one processor; and at least one memory including program code which when executed by the at least one processor results in operations comprising:

generating a feature vector including one or more independent components from transcranial magnetic stimulation electroencephalogram data collected during a transcranial magnetic stimulation procedure, the feature vector including a source activity features that includes a complexity of a source pattern associated with the one or more independent components;

applying a machine learning model to identify, based at least on the feature vector, one or more artefactual independent components comprising the transcranial magnetic stimulation electroencephalogram data collected during the transcranial magnetic stimulation procedure;

generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, real-time adjustments to one or more parameters of the transcranial magnetic stimulation procedure.

29. A system, comprising:

at least one processor; and at least one memory including program code which when executed by the at least one processor results in operations comprising:

generating a feature vector including one or more independent components from transcranial magnetic stimulation electroencephalogram data collected during a transcranial magnetic stimulation procedure, the feature vector including a maximum magnitude feature that includes a maximum voltage differential that is recorded across a plurality of trials of transcranial magnetic stimuli that are administered during the transcranial magnetic stimulation procedure, and wherein each trial of transcranial magnetic stimuli comprises an administration of a single transcranial magnetic stimulation pulse, a pair of transcranial magnetic stimulation pulses, and/or a train of transcranial magnetic stimulation pulses;

applying a machine learning model to identify, based at least on the feature vector, one or more artefactual independent components comprising the transcranial magnetic stimulation electroencephalogram data collected during the transcranial magnetic stimulation procedure;

generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, real-time adjustments to one or more parameters of the transcranial magnetic stimulation procedure.

30. A system, comprising:

at least one processor; and at least one memory including program code which when executed by the at least one processor results in operations comprising:

generating a feature vector including one or more independent components from transcranial magnetic stimulation electroencephalogram data collected during a transcranial magnetic stimulation procedure, the feature vector including a short-time magnitude feature that includes one or more transcranial magnetic stimulation-evoked potential peaks present in the one or more independent components, and wherein the one or more transcranial magnetic stimulation-evoked potential peaks are identified by at least determining a mean magnitude of voltage differentials recorded over a plurality of time windows;

applying a machine learning model to identify, based at least on the feature vector, one or more artefactual independent components comprising the transcranial magnetic stimulation electroencephalogram data collected during the transcranial magnetic stimulation procedure;

generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, real-time adjustments to one or more parameters of the transcranial magnetic stimulation procedure.

31. A system, comprising:
at least one processor; and
at least one memory including program code which when executed by the at least one processor results in operations comprising:
generating a feature vector including one or more independent components from transcranial magnetic stimulation electroencephalogram data collected during a transcranial magnetic stimulation procedure, the feature vector including a skewness feature that includes a measure of asymmetry in a probability distribution of the transcranial magnetic stimulation electroencephalogram data;
applying a machine learning model to identify, based at least on the feature vector, one or more artefactual independent components comprising the transcranial magnetic stimulation electroencephalogram data collected during the transcranial magnetic stimulation procedure;
generating clean transcranial magnetic stimulation electroencephalogram data by at least removing, from the transcranial magnetic stimulation electroencephalogram data, the one or more artefactual independent components; and
performing, based at least on the clean transcranial magnetic stimulation electroencephalogram data, real-time adjustments to one or more parameters of the transcranial magnetic stimulation procedure.

32. A system, comprising:
at least one processor; and
at least one memory including program code which when executed by the at least one processor results in operations comprising:
generating a feature vector including one or more independent components from transcranial magnetic stimulation electroencephalogram data collected during a transcranial magnetic stimulation procedure, the feature vector including a band-power feature that includes a band-power for a theta band between 4 Hertz and 7 Hertz, an alpha band between 8 Hertz and 12 Hertz, a beta band between 13 Hertz and 30 Hertz, and/or a gamma band between 31 Hertz and 50 Hertz;
applying a machine learning model to identify, based at least on the feature vector, one or more artefactual independent components comprising the transcranial magnetic stimulation electroencephalogram data collected during the transcranial magnetic stimulation procedure;
generating clean transcranial magnetic stimulation electroencephalogram data by at least removing, from the transcranial magnetic stimulation electroencephalogram data, the one or more artefactual independent components; and
performing, based at least on the clean transcranial magnetic stimulation electroencephalogram data, real-time adjustments to one or more parameters of the transcranial magnetic stimulation procedure.

33. A system, comprising:
at least one processor; and
at least one memory including program code which when executed by the at least one processor results in operations comprising:
generating a feature vector including one or more independent components from transcranial magnetic stimulation electroencephalogram data collected during a transcranial magnetic stimulation procedure, the feature vector including an electroencephalogram spectral feature that includes a value of a parameter b in the equation $y=(a/f^b)+c (b>0)$;
applying a machine learning model to identify, based at least on the feature vector, one or more artefactual independent components comprising the transcranial magnetic stimulation electroencephalogram data collected during the transcranial magnetic stimulation procedure;
generating clean transcranial magnetic stimulation electroencephalogram data by at least removing, from the transcranial magnetic stimulation electroencephalogram data, the one or more artefactual independent components; and
performing, based at least on the clean transcranial magnetic stimulation electroencephalogram data, real-time adjustments to one or more parameters of the transcranial magnetic stimulation procedure.

34. A system, comprising:
at least one processor; and
at least one memory including program code which when executed by the at least one processor results in operations comprising:
generating a feature vector including one or more independent components from transcranial magnetic stimulation electroencephalogram data collected during a transcranial magnetic stimulation procedure, the feature vector including an electroencephalogram spectral feature that includes a mean fit error between an actual spectrum of the one or more independent components and a fitted shape of an electroencephalogram spectrum within an alpha band between 8 Hertz and 12 Hertz;
applying a machine learning model to identify, based at least on the feature vector, one or more artefactual independent components comprising the transcranial magnetic stimulation electroencephalogram data collected during the transcranial magnetic stimulation procedure;
generating clean transcranial magnetic stimulation electroencephalogram data by at least removing, from the transcranial magnetic stimulation electroencephalogram data, the one or more artefactual independent components; and
performing, based at least on the clean transcranial magnetic stimulation electroencephalogram data, real-time adjustments to one or more parameters of the transcranial magnetic stimulation procedure.

35. A system, comprising:
at least one processor; and
at least one memory including program code which when executed by the at least one processor results in operations comprising:
preprocessing transcranial magnetic stimulation electroencephalogram data collected during a transcranial magnetic stimulation procedure by at least epoching the transcranial magnetic stimulation electroencephalogram data and/or re-referencing the transcranial magnetic stimulation electroencephalogram data with respect to a common average;
applying a machine learning model to identify one or more artefactual independent components comprising the preprocessed transcranial magnetic stimulation electroencephalogram data;

generating clean transcranial magnetic stimulation electroencephalogram data by at least removing, from the transcranial magnetic stimulation electroencephalogram data, the one or more artefactual independent components; and performing, based at least on the clean transcranial magnetic stimulation electroencephalogram data, adjustments to one or more parameters of the transcranial magnetic stimulation procedure.

* * * * *